(12) United States Patent
Poland et al.

(10) Patent No.: US 12,290,401 B2
(45) Date of Patent: May 6, 2025

(54) HANDHELD ULTRASOUND SCANNER WITH DISPLAY RETENTION AND ASSOCIATED DEVICES, SYSTEMS, AND METHODS

(71) Applicant: KONINKLIJKE PHILIPS N.V., Eindhoven (NL)

(72) Inventors: McKee Dunn Poland, Andover, MA (US); James Christopher Taylor, State College, PA (US); Sean Joseph Kyne, Brookline, MA (US); Elaina Mansur, Chelmsford, MA (US); Richard Allan Hager, Derry, NH (US); Bernard Joseph Savord, Andover, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 171 days.

(21) Appl. No.: 17/908,016

(22) PCT Filed: Mar. 3, 2021

(86) PCT No.: PCT/EP2021/055269
§ 371 (c)(1),
(2) Date: Aug. 30, 2022

(87) PCT Pub. No.: WO2021/175895
PCT Pub. Date: Sep. 10, 2021

(65) Prior Publication Data
US 2023/0101257 A1 Mar. 30, 2023

Related U.S. Application Data

(60) Provisional application No. 62/985,566, filed on Mar. 5, 2020.

(51) Int. Cl.
*A61B 8/00* (2006.01)

(52) U.S. Cl.
CPC ............ *A61B 8/4427* (2013.01); *A61B 8/462* (2013.01)

(58) Field of Classification Search
CPC ............................. A61B 8/4427; A61B 8/462
See application file for complete search history.

(56) References Cited

U.S. PATENT DOCUMENTS

| 5,617,866 A | 4/1997 | Marian, Jr. |
| 6,491,636 B2 | 12/2002 | Chenal et al. |

(Continued)

FOREIGN PATENT DOCUMENTS

| DE | 102013107816 A1 | 1/2015 |
| JP | 2003299647 A | 10/2003 |

(Continued)

OTHER PUBLICATIONS https://www.amazon.com/Hukado-Adjustable-Flashlight-Keychains-Multi-Color/dp/B07RN4QKVH/ref=sr_1_2_sspa?crid=BDFW5ACDYVE1&dib=eyJ2ljoiMSJ9.pzkK4jPLbaVnEmHTbyHsTulLCfflqH1nG0rkxo2hhH4-QU0tVAysAkg4gyyYN9rb4Y_XQMcEh2Kdwd8xjEX7CYRxv3dJjOD_0aailcFIXsevk18cpQm90rqHX01Ficwns30D7IC1qVeQM7gP9wPPbx (Year: 2019).*

(Continued)

*Primary Examiner* — Dixomara Vargas

(57) ABSTRACT

Handheld ultrasound devices with display-retaining designs that allow the processor/display assembly to be removed and/or repositioned are provided. According to one embodiment, a handheld ultrasound scanning device includes a main body housing having a first side and a second side. An ultrasound transducer is coupled to the second side and is configured to obtain ultrasound data. A communication interface is communicatively coupled to the ultrasound transducer and configured to transmit the ultrasound data obtained by the ultrasound transducer to a processor and (Continued)

display assembly. The first side of the main body housing includes a retention feature that is configured to retain the processor and display assembly in contact with the main body housing at a position and orientation relative to the main body housing.

19 Claims, 15 Drawing Sheets

(56) References Cited

U.S. PATENT DOCUMENTS

| | | | |
|---|---|---|---|
| 6,635,019 | B2 | 10/2003 | Davidsen |
| 7,074,188 | B2 | 7/2006 | Nair et al. |
| 7,175,597 | B2 | 2/2007 | Vince et al. |
| 7,551,758 | B2 | 6/2009 | Florent et al. |
| 2003/0097071 | A1 | 5/2003 | Halmann et al. |
| 2005/0148873 | A1 | 7/2005 | Petersen et al. |
| 2009/0024039 | A1* | 1/2009 | Wang ............... A61B 10/0233 600/459 |
| 2010/0016726 | A1 | 1/2010 | Meier |
| 2010/0249598 | A1 | 9/2010 | Smith et al. |
| 2011/0077557 | A1* | 3/2011 | Wing ............... A61B 8/546 601/2 |
| 2014/0085603 | A1* | 3/2014 | Su ............... A61B 3/12 351/206 |
| 2014/0300720 | A1 | 10/2014 | Rothberg |
| 2017/0035352 | A1 | 2/2017 | Appleby |
| 2018/0014811 | A1* | 1/2018 | Sonnenschein ...... A61B 8/4245 |
| 2018/0374604 | A1* | 12/2018 | Yang ............... H05K 1/0296 |
| 2020/0029837 | A1* | 1/2020 | Joudi ............... A61B 5/0086 |
| 2020/0323517 | A1* | 10/2020 | Zahiri ............... A61B 8/485 |
| 2021/0282747 | A1 | 9/2021 | Poland |
| 2021/0315541 | A1 | 10/2021 | Poland |
| 2021/0369297 | A1* | 12/2021 | Burkett ............... A61M 25/06 |

FOREIGN PATENT DOCUMENTS

| | | |
|---|---|---|
| JP | 2014150936 A | 8/2014 |
| WO | 2010064156 A1 | 6/2010 |
| WO | 2014077606 A1 | 5/2014 |
| WO | 2016083985 A1 | 6/2016 |
| WO | 2017150484 A1 | 9/2017 |

OTHER PUBLICATIONS

International Search Report and Written Opinion for PCT/EP2021/055269; Mailing date: Jun. 24, 201, 11 pages.

* cited by examiner

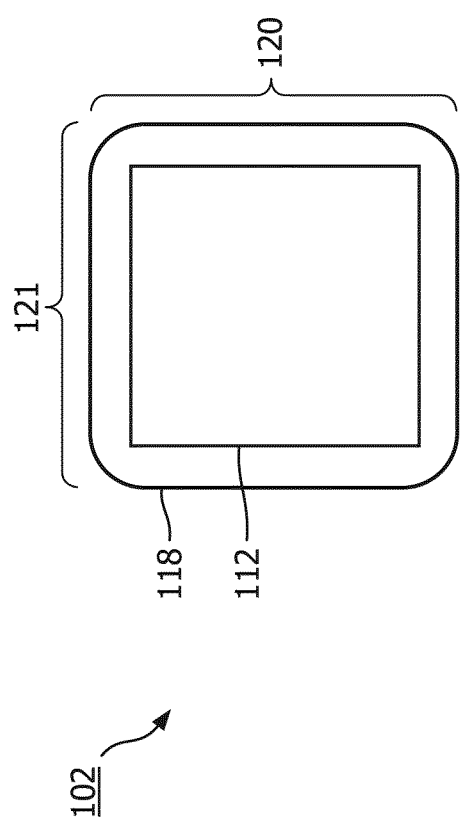
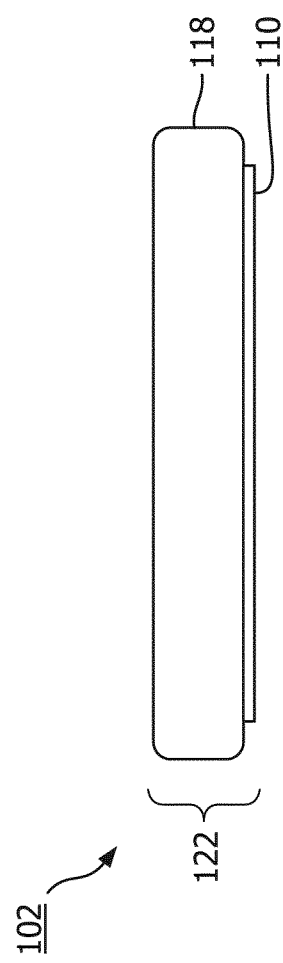

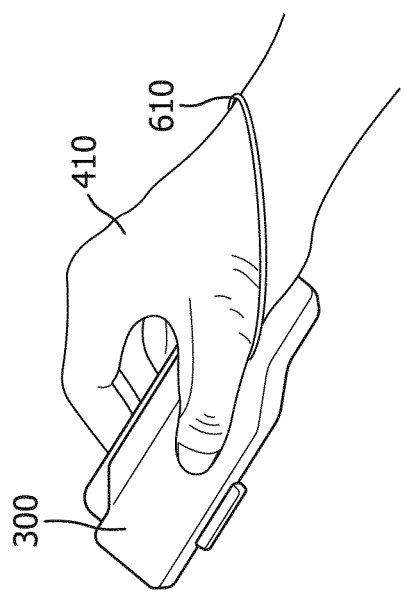
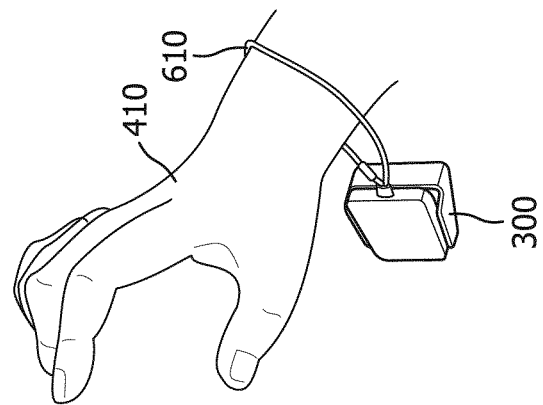
FIG. 7A
FIG. 7B

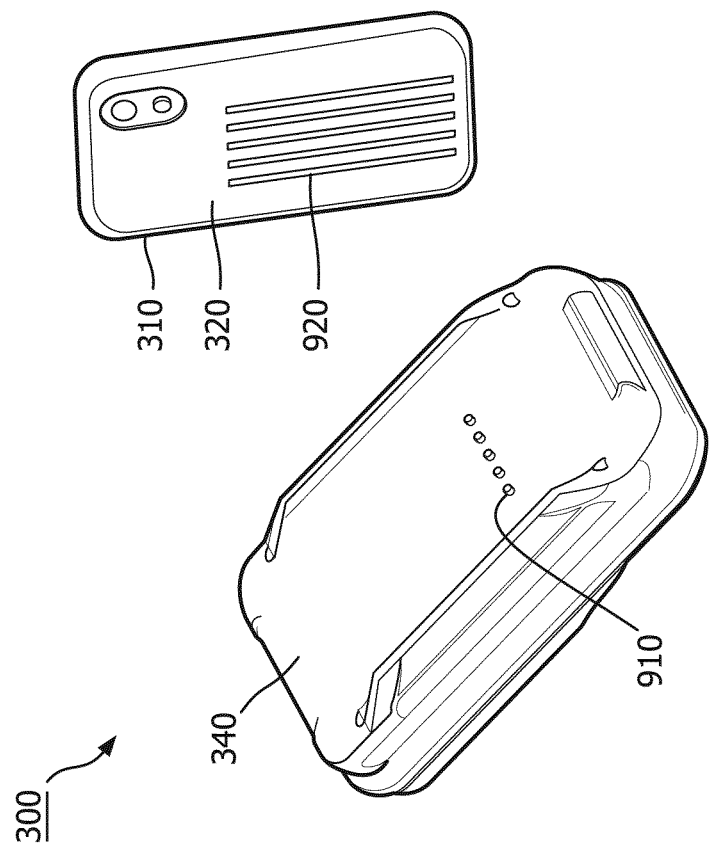
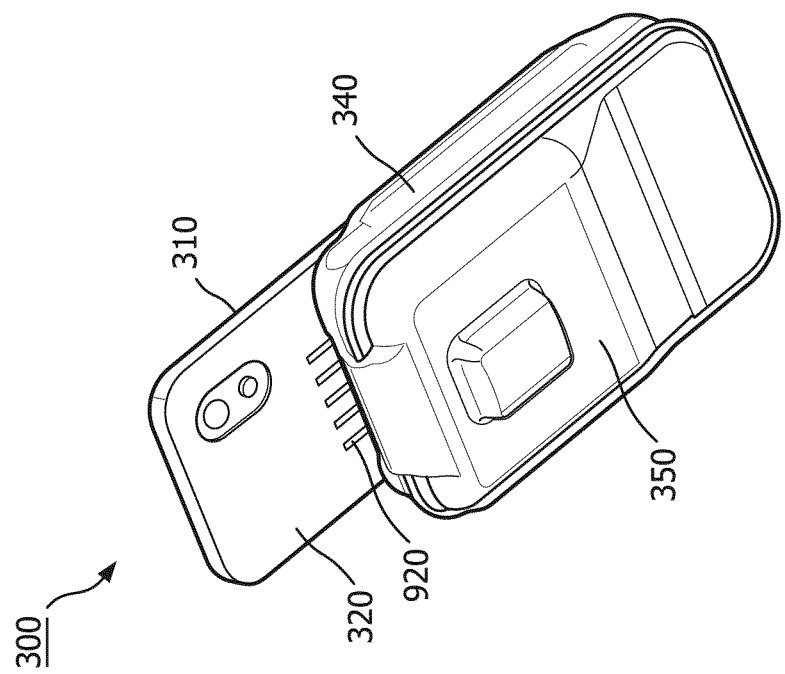
FIG. 10B
FIG. 10A

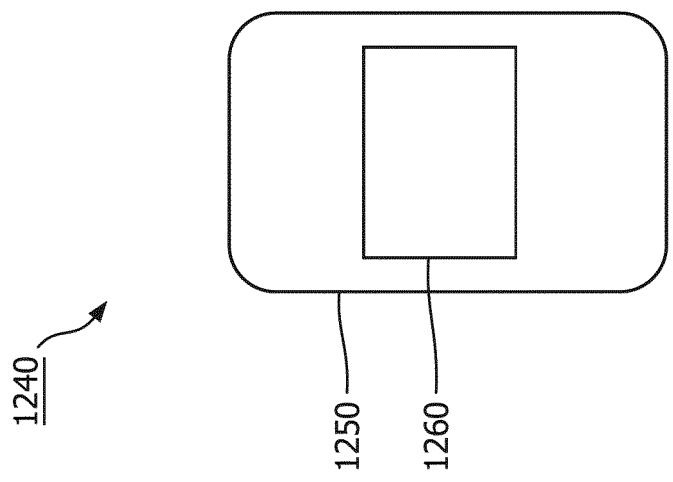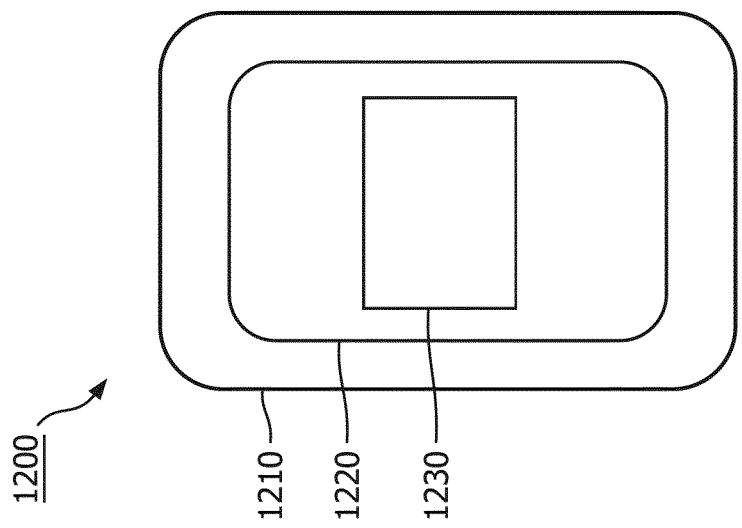
FIG. 12

HANDHELD ULTRASOUND SCANNER WITH DISPLAY RETENTION AND ASSOCIATED DEVICES, SYSTEMS, AND METHODS

CROSS-REFERENCE TO PRIOR APPLICATIONS

This application is the U.S. National Phase application under 35 U.S.C. § 371 of International Application No. PCT/EP2021/055269, filed on Mar. 3, 2021, which claims the benefit of U.S. Provisional Patent Application No. 62/985,566, filed on Mar. 5, 2020. These applications are hereby incorporated by reference herein.

TECHNICAL FIELD

The subject matter described herein relates to handheld medical scanning devices; in particular, to a handheld ultrasound imaging device with a removable, repositionable display and processor. This handheld imaging device has particular but not exclusive utility for diagnostic medical imaging procedures.

BACKGROUND

As medical technology has advanced, several different imaging modalities, e.g., magnetic resonance imaging (MRI), computed tomography (CT), x-ray, fluoroscopy, angiography, ultrasound, etc., have been developed to allow physicians to view anatomical structures within a patient's body without having to open the patient surgically. In the case of ultrasound, ultrasonic waves are emitted from ultrasonic transducers into the patient's body. The ultrasonic waves are partially reflected by discontinuities arising from tissue structures, red blood cells, and other features within the patient. Echoes from the reflected waves are received by the ultrasonic transducers and processed to produce an ultrasonic image. The ultrasonic image is generally output to a display for viewing by a physician. Review of the displayed images often plays an integral role in a physician's diagnosis and treatment plan.

Handheld ultrasound systems on the market today typically include a handheld probe and a separate computer/display, typically connected by an electrical cable carrying power and acoustic signals. Some wireless, battery operated probes connect to a display computer via WiFi or proprietary radio link, but again the display remains separate from the probe. Existing integrated ultrasound units with small, low-resolution displays built into the probe are known in the art, but suffer from a variety of drawbacks including ergonomics, display size, and image quality.

The information included in this Background section of the specification, including any references cited herein and any description or discussion thereof, is included for technical reference purposes only and is not to be regarded as subject matter by which the scope of the disclosure is to be bound.

SUMMARY

Embodiments of the present disclosure describe a handheld ultrasound system that integrates an ultrasound transducer, a signal path, and a processor/display assembly in a display-retaining design that allows the processor/display assembly to be removed and/or repositioned. The processor/display assembly can be coupled to a display retention region of the scanner body such that it can be repositioned for optimal viewing or removed entirely for separated viewing. The processor/display assembly (e.g., a smartphone running specialized software) may be connected to the signal path in the scanner housing via a short USB cable by pogo spring pins, and/or by a wireless link. The flexibility afforded by its repositioning makes the system suitable for many clinical applications. The system may be hereinafter referred to as a handheld ultrasound system with display retention.

According to one embodiment, a handheld ultrasound scanning device includes: a main body housing configured for handheld use. The main body housing comprises a first side and a different second side; an ultrasound transducer coupled to the second side of the main body housing and configured to obtain ultrasound data; and a communication interface communicatively coupled to the ultrasound transducer and configured to transmit the ultrasound data obtained by the ultrasound transducer to a processor and display assembly configured to display ultrasound images representative of the ultrasound data. The first side of the main body housing includes one or more retention features at least partially around a retention region. The retention region is sized and shaped to receive the processor and display assembly, and the one or more retention features are configured to retain the processor and display assembly in contact with the main body housing at a position and orientation relative to the main body housing, such that the processor and display assembly can be removed from the retention region.

In some embodiments, the handheld ultrasound scanning device further comprises the processor and display assembly, wherein the processor and display assembly comprises a smartphone or tablet computer. In some embodiments, the one or more retention features are configured to slidably retain the processor and display assembly such that the processor and display assembly can be repositioned at a plurality of positions relative to the main body housing. In some embodiments, the one or more retention features slidably retain the processor and display assembly such that the processor and display assembly can be repositioned to expose a camera of the processor and display assembly. In some embodiments, the one or more retention features comprise a stop positioned to arrest sliding of the processor and display assembly in a first direction while permitting the sliding of the processor and display assembly in an opposite second direction. In some embodiments, the stop comprises a retention lip. In some embodiments, the one or more retention features comprise a plurality of rails projecting from the first side of the main body housing and positioned on opposing sides of the retention region. In some embodiments, at least one rail comprises a retention lip or a curved inner surface matched to an outer surface of the processor and display assembly.

In some embodiments, the one or more retention features comprise one or more magnets, and the processor and display assembly comprises a magnetically attractable material. In some embodiments, the one or more retention features comprise a magnetically attractable material, and the processor and display assembly comprises one or more magnets. In some embodiments, the communication interface is configured to maintain communication with the processor and display assembly when the processor and display assembly is received within the retention region and when the processor and display assembly is removed from the retention region. In some embodiments, the handheld ultrasound scanning device further comprises a cable coupling the main body housing to the processor and display assembly. IN some embodiments, the cable is connected to a first socket in the main body housing to form a first connection, and the cable is connected to a second socket in the processor and display assembly to form a second connection. In some embodiments, the cable comprises a length that wraps around a wrist of a user when connected to the first socket and the second socket. In some embodiments, the first connection of the cable and the first socket comprises a first retention force. In some embodiments, the second connection of the cable and the second socket comprises a second retention force. In some embodiments, the first retention force and the second retention force exceed a weight of the handheld ultrasound scanning device.

In some embodiments, the communication interface comprises at least one of a conductive pin or a conductive trace configured to be in electrical communication with at least one of a conductive trace or a conductive pin of the processor and display assembly. In some embodiments, the communication interface is configured to transmit the ultrasound data to the processor and display assembly by a wireless link. In some embodiments, the handheld ultrasound scanning device further comprises an ultrasound transducer cartridge comprising a cartridge body removably coupled to the second side of the main body housing. In some embodiments, the ultrasound transducer is coupled to a side of the cartridge body. In some embodiments, the cartridge body is configured to form a moisture- and dust-resistant enclosure with the main body housing. In some embodiments, the handheld ultrasound scanning device further comprises processing circuitry contained within the main body housing and communicatively coupled to the communication interface and the ultrasound transducer.

According to another embodiment of the present disclosure, a handheld ultrasound imaging device includes a main body housing configured for handheld use. The main body housing comprises: two or more side rails protruding from a front surface of the main body housing and positioned on opposing sides of a retention region, wherein the retention region is configured to receive a processor and display assembly; a communication interface configured to establish an electrical connection with a corresponding plurality of conductive traces coupled to the processor and display assembly when the processor and display assembly is positioned within the retention region; and processing circuitry contained within the main body housing and communicatively coupled to the communication interface; and an ultrasound transducer cartridge coupled to a rear surface of the main body housing, wherein the ultrasound transducer cartridge comprises an ultrasound transducer positioned on a rear side of the ultrasound transducer cartridge. The ultrasound transducer is configured to emit ultrasonic energy and provide, to the processing circuitry, ultrasound imaging signals representative of echoes of the ultrasonic energy, and the processing circuitry is configured to perform signal processing on the ultrasound imaging signals to provide image data to the processor and display assembly.

The handheld ultrasound system with display retention feature disclosed herein has particular, but not exclusive, utility for diagnostic medical imaging in clinician offices and informal settings (e.g., homes, rural/remote locations (telemedicine) military (deployed with medics), and pre-hospital settings).

According to another embodiment of the present disclosure, a handheld ultrasound scanning device includes a main body, a sensor cartridge and a processor and display assembly. The main body housing is configured for handheld use, wherein the main body housing comprises a first side and a different second side, the first side comprising a first electrical connector and a first mechanical connector. The sensor cartridge may be configured to removably couple with the first side of the main body housing, the sensor cartridge comprising a second electrical connector and a second mechanical connector. The second electrical connector mates with the first electrical connector and the second mechanical connector mates with the first mechanical connector. The sensor cartridge further comprises a transducer configured to send and receive ultrasound signals and circuitry configured to process the received ultrasound signals and transfer the processed signals to the main body housing via the first and second electrical connectors. The processor and display assembly is coupled to the second side of the main body housing and configured to receive the processed signals, generate a clinical parameter from the processed signals, and display the clinical parameter to a user of the handheld ultrasound system. The clinical parameter may include an image, a measurement or both.

This Summary is provided to introduce a selection of concepts in a simplified form that are further described below in the Detailed Description. This Summary is not intended to identify key features or essential features of the claimed subject matter, nor is it intended to limit the scope of the claimed subject matter. A more extensive presentation of features, details, utilities, and advantages of the handheld ultrasound system with display retention, as defined in the claims, is provided in the following written description of various embodiments of the disclosure and illustrated in the accompanying drawings.

BRIEF DESCRIPTION OF THE DRAWINGS

Illustrative embodiments of the present disclosure will be described with reference to the accompanying drawings, of which:

FIG. 1A is an elevation view of a handheld medical scanning device, according to aspects of the present disclosure FIG. 1B is a side elevation view of a handheld medical scanning device, according to aspects of the present disclosure.

FIG. 7A is a perspective view of a handheld ultrasound system with display retention and a cable acting as a lanyard, in accordance with at least one embodiment of the present disclosure.

FIG. 7B is a perspective view a handheld ultrasound system with display retention and a cable acting as a lanyard, in accordance with at least one embodiment of the present disclosure.

FIG. 10A is a perspective view of a rear side of a handheld ultrasound system with a removable press-fit display, in accordance with at least one embodiment of the present disclosure.

FIG. 10B is a perspective view of a front side of a handheld ultrasound system with a removable press-fit display, in accordance with at least one embodiment of the present disclosure.

FIG. 12 is an elevation view of a handheld medical scanning device and display case, according to aspects of the present disclosure.

DETAILED DESCRIPTION

Figure 2:
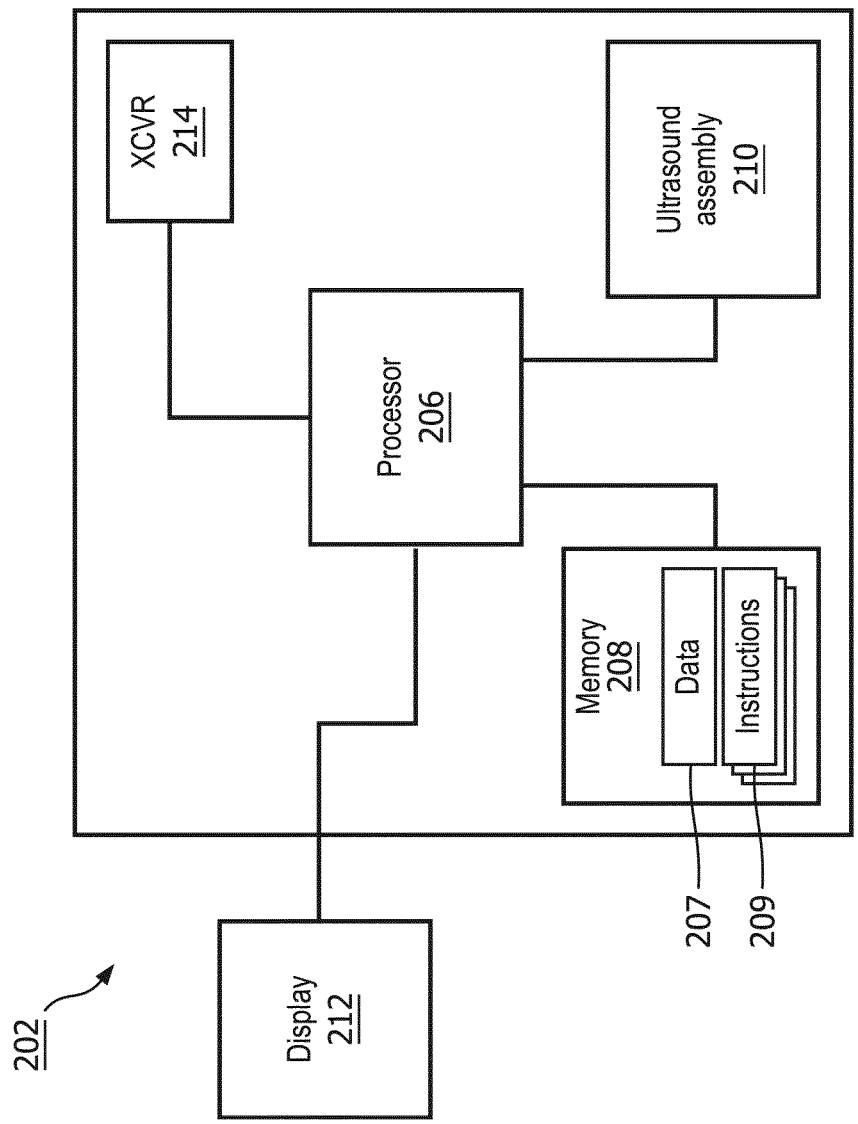
FIG. 2 is a diagrammatic schematic view of a handheld medical scanning device, according to aspects of the present disclosure.

Embodiments of the present disclosure describe a handheld ultrasound system that includes a sensor, a signal path, and a processor/display assembly in a design that allows the processor/display assembly to be repositioned. The processor/display assembly slides or presses into a channel within a front surface of the scanner body, so that it can be repositioned or removed entirely for separated viewing. The processor/display assembly (e.g., an Android phone, iPhone, tablet, phablet, PDA, or other smart handheld device) may be connected to the signal path in the scanner housing via a short cable (e.g., a universal serial bus (USB) cable), by spring-loaded pogo pins, or by a wireless link. The flexibility afforded by repositioning of the processor/display assembly makes the system suitable for a wide variety of clinical applications.

The system, which may be referred to as a handheld ultrasound system with display retention, advantageously provides numerous simultaneous capabilities, including high-quality imaging capability, with a high-resolution display integrated into the probe, to allow single-handed, simultaneous scanning and viewing. As described further below, the display retention may comprise one or more structural features that are configured to retain a processor/display assembly in a repositionable and/or removable arrangement relative to a housing. In some embodiments, the display retention comprises one or more structural features that allow the processor/display assembly to be slid into, locked into, clamped to, or otherwise physically coupled to a retention region of a housing or body. In some aspects, the display retention slidably retains the processor/display assembly at a position and orientation relative to a display retention region of the device. In other words, the display retention features can maintain the processor/display assembly in place and still allow a sliding motion of the processor/display assembly. In an exemplary embodiment, the display retention comprises a press-fit feature as described further below. Accordingly, the system may also be referred to as a handheld ultrasound system with press-fit display, in some embodiments. In other embodiments, the display may be retained with magnets (e.g., a magnet coupled to one of the display and the main sensor body, and a steel plate coupled to the other), and the system may be referred to as a handheld ultrasound system with magnetic display retention. The system also provides the ability to reposition the integrated processor/display assembly with respect to the probe sensor and with respect to the user's hand that is manipulating the scanner. The system additionally provides the ability to separate the processor/display assembly, at will, temporarily, from the handheld probe to allow independent display operation. The combination of all three capabilities creates a system that advantageously allows single handed scanning in a variety of clinical scenarios, with the flexibility to adapt to clinicians' hand size and ergonomic preferences.

In an exemplary embodiment, the handheld ultrasound system with display retention includes three mutually separable components: (1) a front-facing processor/display assembly, connected either wirelessly or via cable (e.g., USB cable) to the main scanner body, (2) a main scanner body in the middle of the device containing the image acquisition and data acquisition electronics, and (3) a rear-facing sensor assembly that can be removed and replaced with a different sensor assembly via a novel cartridge system. However, in some embodiments, two or more of the components mentioned above are not separable. For example, in one embodiment, the main scanner body and the downward facing sensor assembly may comprise an integral unit comprising a single housing.

The present disclosure advantageously describes the physical interaction between the first two components, the processor/display assembly and the main scanner body. The handheld ultrasound system with display retention provides an attachment area on the front of the main scanner body for the processor/display assembly. In an exemplary embodiment, a small smartphone can be pressed into a display retention region between one or more raised portions (e.g., side rails) on the front of the device. The smartphone (e.g., a Palm Companion) may run specialized software (e.g., the Philips Lumify® ultrasound software application for smartphones and tablets, including the telemedicine feature called Reacts™), through which it can be wirelessly connected to a health network for patient data exchange, image data exchange, and telemedicine. The smartphone connects to the main body of the scanner via an electrical cable (e.g., USB, ethernet) so that it can control the acquisition signal path and receive image data. Alternatively, the smartphone can be connected by means of pogo pins on the front surface of the main scanner body, and conductive strips (e.g., steel, copper, or gold foil strips) on the back surface of the phone case, eliminating the short cable. Alternatively, a wireless connection (e.g., Bluetooth, WiFi, near field communication (NFC), ultra-wide band (UWB), millimeter wave, etc.) can be employed for data transfer between the smartphone and the main scanner body, and/or for transfer between the phone and a host system.

The present disclosure aids substantially in medical imaging, particularly in informal settings, by improving the versatility of ultrasound scanners intended for single-handed operation. Implemented on a smartphone in communication with a scanner body and sensor cartridge, the handheld ultrasound system with display retention disclosed herein provides practical one-handed imaging operation with a repositionable display. This improved work flow transforms an operation requiring two hands and multiple surfaces into a one-handed task that can be performed in conjunction with other activities, including but not limited to manual note taking, moving the patient, administering medications, manipulating other medical devices, etc., without holding separate scanner and display/computing devices. This unconventional approach improves the functioning of the ultrasound imaging system by employing commercially-available mobile computing devices with high-resolution color displays that can be operated one-handedly by a wide variety of different users.

The imaging, measurement, and/or diagnostic software may be implemented as a smartphone app viewable on a smartphone display, and operated by a control process executing on the smartphone processor that accepts user inputs from a touchscreen interface and/or button interface, and that is in communication with one or more imaging sensors. In that regard, the control process performs certain specific operations in response to different inputs or selections made at different times. Certain structures, functions, and operations of the processor, display, sensors, and user input systems are known in the art, while others are recited herein to enable novel features or aspects of the present disclosure with particularity.

These descriptions are provided for exemplary purposes only, and should not be considered to limit the scope of the handheld ultrasound system with display retention. Certain features may be added, removed, or modified without departing from the spirit of the claimed subject matter.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1A and FIG. 1B show an elevation view and a side elevation view, respectively, of a handheld medical scanning device 102, according to aspects of the present disclosure. As illustrated, the handheld medical scanning device 102 may include an imaging element 110, a display 112, and a housing 118. The housing 118 may have a length 120, width 121, and depth 122. The display 112 and the imaging element 110 may be disposed on any surface or face of the handheld medical scanning device 102, including the front, rear, and side faces of the handheld medical scanning device 102. Further, the display 112 and/or the imaging element may be wholly or partially disposed within the housing 118. Additional aspects of the handheld medical scanning device 102 and the various features thereof will be described in greater detail below.

The handheld medical scanning device 102 is sized and shaped for handheld use. Though variously illustrated as having the perimeter of a square or rounded square, the handheld medical scanning device 102 may in some cases have a circular perimeter, a triangular perimeter, a rectangular perimeter, a pentagonal perimeter, a hexagonal perimeter, or any other suitable shape and/or combinations thereof. The housing 118 comprises a length 120, width 121, and depth 122. The length, 120, width 121, and/or depth 122 may be suitable to allow the handheld medical scanning device 102 to be used with a single hand grip by a variety of different clinicians or other users.

The handheld medical scanning device may be sized, shaped, and structurally arranged such that a user may maintain a single-hand grip on the handheld medical scanning device 102 by gripping the handheld medical scanning device 102 with their thumb on one lateral face of the housing 118 and their index finger on an opposing lateral face of the housing 118. The lateral faces may be thick enough, and the other dimensions small enough, that a natural way to hold the handheld medical scanning device 102 is by its lateral faces. A user's hand may partially enclose the handheld medical scanning device such that the user's thumb, interdigital webbing, and forefinger touch three of the four sides of the handheld medical scanning device to form a comfortable grip. When the handheld medical scanning device 102 is held in this way, the display 112 may be viewable by a user while the imaging element 110 is pressed against a patient's body. In some embodiments, at least part of the housing or display of the handheld medical device may include capacitive touch sensors, or other touch sensors, such that the presence or location of fingers or hand webbing may be detected.

The display 112 may comprise a screen or monitor, which may comprise a capacitive or resistive touch screen, and may serve as a graphical user interface (GUI). In other instances, the display 112 may comprise one or more indicator lights, e.g., a red light and a green light. The display 112 may partially or wholly form a surface of the handheld medical scanning device 102. In some aspects, the display 112 may be part of a display unit. The display unit may comprise the display 112 and circuitry connecting the display 112 to a processor of the handheld medical scanning device 102. One or more components of the display unit may be wholly or partially disposed within the housing 118.

The handheld medical scanning device 102 may be battery powered and may comprise one or more batteries. Said batteries may be disposed within the handheld medical scanning device 102 and may be removeable. In some instances, batteries powering the handheld medical scanning device 102 may be rechargeable. For example, the batteries of the handheld medical scanning device 102 may be recharged by mating the handheld medical scanning device 102 with a docking station, by mating the handheld medical scanning device 102 with a power cord plugged into an electrical outlet, etc. In some cases, the handheld medical scanning device 102 may be powered by a power cord plugged into an electrical outlet. The power cord may be used, for example, when the batteries are dead or absent, in order to preserve battery life, etc. The power cord may also be used in instances in which the handheld medical scanning device 102 is not configured to support battery power.

The handheld medical scanning device 102 may be operable to obtain data, for example, ultrasound data, representative of a patient's anatomy via the imaging element 110. In that regard, the handheld medical scanning device 102 may be operable to image the patient's anatomy via the imaging element. For example, the imaging element 110 may be placed in contact with or in proximity to a patient's skin overlying an area to be imaged. The imaging element 110 may then emit one or more types of energy (e.g., ultrasonic waves) and receive energy (e.g., ultrasonic echoes) reflected by the patient's bodily structures. This reflected energy may be used to form images of the patient's anatomy and/or to facilitate assessment of one or more anatomical structures. In some instances, instead of displaying or processing the ultrasound data to form an image, the data is processed to provide a non-image clinical indication—such as a measurement that provides a clinical indication within the data set. The measurement may be the presence or absence of a feature within the ultrasound data. In additional embodiments, the measurement may be a calculated score or parameter from the ultrasound data.

As used herein, imaging may refer to the process of scanning with one or more types of energy, e.g., ultrasonic waves, irrespective of whether reflected energy is used to form images. For example, scanning a patient's anatomy with ultrasonic waves in order to obtain data representative of the patient's anatomy, e.g., data which may be used in assessment of an anatomical structure, may be referred to as imaging even if an ultrasound image is not generated based on the obtained data. In that regard, conjugations of "imaging" can be referenced as corresponding conjugations of "scanning," "imaging data" as "scanning data," "imaging preset" as "scanning preset," "imaging procedure" as "scanning procedure," "imaging modality" as "scanning modality," "image collection" as "data collection," "imaging angle" as "scanning angle," "imaging depth" as "scanning depth," "imaging target" as "scanning target," "imaging plane" as "scanning plane," "imaging location" as "scanning location," etc.

The imaging element 110 may comprise an infrared scanner, an ultrasound assembly, e.g., an ultrasound scanner, an optical imaging element, an Optical Coherence Tomography (OCT) scanner, a Computed Tomography (CT) scanner, an X-Ray scanner, or combinations thereof. Accordingly, the handheld medical scanning device 102 may obtain any combination of thermal images, ultrasound images, which may comprise three dimensional (3D) ultrasound images, optical images, OCT images, CT images, and X-ray images. In particular, for embodiments in which the imaging element 110 comprises an ultrasound scanner, the imaging element 110 may comprise one or more ultrasound transducers configured to emit ultrasonic waves into the bodily tissues of the patient. In some aspects, ultrasound transducers may be referenced as acoustic elements. The ultrasonic waves may be partially reflected by discontinuities arising from tissue structures, red blood cells, and other features within the patient. Echoes from the reflected ultrasonic waves may be received by the acoustic elements and processed by the handheld medical scanning device 102 to produce an ultrasonic image. In that regard, the handheld medical scanning device 102 can be referenced as an ultrasound imaging device. In some cases, echoes from the reflected ultrasonic waves may be received by the acoustic elements and processed by the handheld medical scanning device 102 to facilitate an assessment of an anatomical structure without an ultrasonic image being produced. In that regard, the handheld medical scanning device 102 can be referenced as an ultrasound scanning device, and the imaging element 110 may be referenced as an ultrasound transducer array or simply as an array.

The imaging element 110 can include one or more acoustic elements. For example, a plurality of acoustic elements can be arranged in an array, e.g., an ultrasound transducer array. For example, an ultrasound transducer array can include any suitable number of individual acoustic elements between 2 acoustic elements and 100,000 acoustic elements, including values such as 2 acoustic elements, 4 acoustic elements, 36 acoustic elements, 64 acoustic elements, 128 acoustic elements, 500 acoustic elements, 812 acoustic elements, 10,000 acoustic elements, 65,000 acoustic elements, and/or other values both larger and smaller. The ultrasound transducer array can be any suitable configuration, such as phased array including a planar array, a curved array, etc. For example, the ultrasound transducer array can be a one-dimensional array, 1.x-dimensional array, such as a 1.5-dimensional array, or a two-dimensional array, in some instances. In that regard, the ultrasound transducer or ultrasound transducer array can be configured obtain one-dimensional, two-dimensional, and/or three-dimensional images of the anatomy of the patient. The ultrasound transducer array can be a matrix array, including one or more segments of ultrasound elements (e.g., one or more rows, one or more columns, and/or one or more orientations) that can be uniformly or independently controlled and activated. The imaging element 110 can include any suitable transducer type, including a piezoelectric micromachined ultrasound transducer (PMUT), capacitive micromachined ultrasonic transducer (CMUT), single crystal, lead zirconate titanate (PZT), PZT composite, other suitable transducer type, and/or combinations thereof.

The ultrasound assembly may comprise a micro-beamformer. The micro-beamformer may comprise an application-specific integrated circuit (ASIC) that is constructed to accept direct physical connection of individual acoustic elements to the ASIC. The connections may, for example, be made through a ball grid array pin field on a printed circuit board, or directly to the surface of the ASIC itself. For each of the individual acoustic elements, there may be time delay circuits within the ASIC that sequence both transmit and receive signals. A proportion of the receive signals may be combined such that the outputs from the micro-beamformer are partially focused analog signals that can be transmitted over a number of signal lines. Combination of the receive signals may advantageously permit the number of signal lines to be substantially reduced from the total acoustic element count. The signals to and from an individual acoustic element may be sequenced with respect to time and position of the individual acoustic element within an overall transducer array. In addition to sequencing of transmit and receive functions the micro-beamformer may also serve to sum receive signals. This method of signal handling enables an entire transducer array to be addressed (via the beam forming circuitry) by a much smaller number of control lines that ultimately connect to the main beamforming signal path. The summation of signals may result in groups of acoustic elements acting as a single transducer. This effective single transducer or patch may comprise acoustic data that is already partially beam-formed. The number of patches may have a direct impact on the number of signal lines that connect to the main beamforming signal path. The micro-beamformer may also perform other functions such as generation of a transmit pulse, and gain control. In some cases, time delay controls may be used to steer and/or focus a beam formed by the micro-beamformer. The extent to which a beam can be focused or steered may be a function of the total number of acoustic elements on either of the orthogonal axes of a transducer array. The following aspects of a transducer array may promote effective beam forming: small individual acoustic elements, which may permit the acoustic elements to receive and transmit ultrasound waves in multiple directions, where smaller acoustic elements afford larger acceptance angles; maximization of array aperture, which may facilitate focusing; and acoustic elements positioned close together, which may reduce grating lobe artifacts.

A clinician or other user of the handheld medical scanning device 102 may input instructions to control the operation of the handheld medical scanning device 102 via one or more physical buttons or switches, through voice activation, and/or via the display 112. In that regard, the display 112 may comprise a capacitive or resistive touch screen and may serve as a graphical user interface (GUI). A user may issue touch-based instructions on the display 112 to switch between various screens, including a home screen, and to magnify one or more regions of an image, e.g., an ultrasound image, which may comprise a 3D ultrasound image, in order to enter one or more preferences (e.g., a brightness preference, in order to input patient information such as a patient's age, weight, sex, medical condition, etc.) in order to access medical data, to activate or deactivate scanning with the imaging element 110, to select an imaging preset, or combinations thereof.

Prior to imaging with the imaging element 110, a user may select one or more imaging presets. Selecting an imaging preset may comprise selecting an anatomical structure to be imaged, e.g., a patient's brain, heart, lungs, stomach, spleen, intestines, bladder, kidneys, bones, teeth, liver, uterus, a tumor within the patient, growths within the patient; etc.; selecting a region to be imaged, e.g., a patient's head, neck, chest, abdomen, groin, upper limbs, lower limbs, extremities, etc., or sections thereof such as a quadrant of a patient's abdomen; selecting some other target to be imaged; selecting an imaging depth; selecting an assessment to be performed, e.g., diagnostic assessment, a length measurement, a width measurement, a thickness or depth measurement, an area measurement, a volume measurement, a heart rate measurement, an efficiency measurement, a flow measurement, an ejection fraction measurement, a density measurement, a measurement of change over time, a weight measurement; an angle measurement; etc.; selecting an imaging modality, e.g., thermal imaging, ultrasound, optical imaging, OCT, CT, X-ray, etc.; selecting an imaging angle; selecting desired view; or any combination thereof.

The combination of selected imaging presets may be referenced as a selected imaging procedure. For example, a user may select an imaging procedure for bladder volume measurement by selecting imaging presets identifying a patient's bladder as an anatomical structure to be imaged and volume measurement as an assessment to be performed. For further example, a user may select an imaging procedure for imaging the left ventricular short axis (SAX) of the heart by selecting imaging presets identifying a patient's heart as an anatomical structure to be imaged and the left ventricular short axis as a desired view. In the event that a user does not select any imaging presets, the user has effectively selected general imaging as the imaging procedure.

A user may begin imaging following selection of an imaging procedure. In some cases, the handheld medical scanning device 102 may begin imaging automatically in response to selection of an imaging procedure. In other cases, a user may manually activate imaging independent of selection of an imaging procedure. Once imaging has begun, the handheld medical scanning device 102 may receive imaging data, e.g., ultrasound imaging data, via the imaging element 110.

In some embodiments, the scanning device 102 includes processing circuitry configured to perform various image processing techniques, such as border detection and pattern recognition. Examples of border detection, image processing, image analysis, and/or pattern recognition include U.S. Pat. No. 7,551,758 entitled "MEDICAL VIEWING SYSTEM AND METHOD FOR DETECTING BORDERS OF AN OBJECT OF INTEREST IN NOISY IMAGES" issued Jun. 23, 2009 with Raoul Florent et al. as inventors, U.S. Pat. No. 6,491,636 entitled "AUTOMATED BORDER DETECTION IN ULTRASONIC DIAGNOSTIC IMAGES" issued Dec. 10, 2002 with Cedric Chenal et al. as inventors, U.S. Pat. No. 7,074,188 entitled "SYSTEM AND METHOD OF CHARACTERIZING VASCULAR TISSUE" issued Jul. 11, 2006 with Anuja Nair, D. Geoffrey Vince, Jon D. Klingensmith and Barry D. Kuban as inventors, U.S. Pat. No. 7,175,597 entitled "NON-INVASIVE TISSUE CHARACTERIZATION SYSTEM AND METHOD" issued Feb. 13, 2007 with D. Geoffrey Vince, Anuja Nair and Jon D. Klingensmith as inventors, U.S. Provisional Patent Application No. 62/699,816, filed Jul. 18, 2018 with McKee Poland as inventor, and U.S. Provisional Patent Application No. 62/699,928, filed Jul. 18, 2018 with McKee Poland as inventor, the teachings of which are hereby incorporated by reference herein in their entirety.

The handheld medical scanning device 102 may track one or more device metrics such as battery life and may modify its behavior based on current metrics. For example, in order to preserve battery life, the handheld medical scanning device 102 may discard some imaging data without first generating and displaying a corresponding image based on the discarded imaging data when the handheld medical scanning device 102 is low on battery even if the handheld medical scanning device 102 would ordinarily display the image prior to discarding the imaging data. Alternatively, or in addition, the handheld medical scanning device may reduce the rate at which it scans the anatomy, producing a lower imaging frame rate, again to reduce power consumption. Battery life may be low when it falls below 50%, below 40%, below 30%, below 25%, below 20%, below 15%, below 10%, below 5%, within 5% of an average amount expended for a selected imaging procedure, within 5% of an average amount expended during a single use, or combinations thereof.

The handheld medical scanning device 102 may provide guidance to a user during imaging. Such guidance may be provided in real time, e.g., as the handheld medical scanning device is obtaining imaging data. In that regard, the handheld medical scanning device 102 may output one or more indications to aid a user in positioning the handheld medical scanning device 102 at a suitable imaging location. A suitable imaging location may be determined based on a selected imaging procedure and/or selected imaging presets defining an imaging procedure. For example, when a patient's heart is selected as an anatomical structure to be imaged, a suitable imaging location may be one at which the handheld medical scanning device 102 can obtain imaging data representative of the patient's heart. In some cases, e.g., when multiple imaging presets have been selected, the ability of the handheld medical scanning device 102 to obtain imaging data representative of a selected anatomical structure may not be sufficient to qualify an imaging location as a suitable imaging location.

The handheld medical scanning device 102 may analyze received imaging data to determine whether or not the handheld medical scanning device 102 is positioned at a suitable imaging location, e.g., by determining whether the received imaging data included imaging data representative of a selected anatomical structure to be imaged. If the handheld medical scanning device 102 determines that it is not positioned at a suitable imaging location, the handheld medical scanning device 102 may output an indication to alert a user to reposition the handheld medical scanning device 102. The indication may comprise one or more of a visual indication, e.g., a picture, an arrow, text, a color, a sign, a symbol, an "X," a light, etc., which may in some cases be displayed on the display 112; an audible indication, e.g., a tone, a chime, a beep, a buzz, a ring, a frequency, etc.; or a tactile indication, e.g., a buzz, a vibration, an electrical pulse, etc.

The handheld medical scanning device 102 may be programmed with and/or may learn information about anatomy, e.g., human and/or animal anatomy, and may store such information in memory such as non-volatile memory. In that regard, the handheld medical scanning device 102 may be able to determine its location based on received imaging data and stored anatomical information. For example, the handheld medical scanning device 102 may determine that a patient's stomach is in view toward a first side of the handheld medical scanning device 102 while the patient's large intestine is in view toward a second side of the handheld medical scanning device 102. In order to bring the patient's bladder into view, e.g., when the patient's bladder is selected as an anatomical structure to be imaged, the handheld medical scanning device 102 may determine, e.g., by consulting stored anatomical information, that the handheld medical scanning device 102 should be moved toward the second side and may output an indication suggesting that the handheld medical scanning device 102 be moved toward the second side.

In some cases, the handheld medical scanning device 102 may automatically adjust the angle of a scan based on the location of the handheld medical scanning device 102 relative to, e.g., an anatomical structure to be imaged. For example, the handheld medical scanning device 102 may adjust the emission of ultrasonic waves such that a scanning angle is adjusted. Such adjustments may be made while the handheld medical scanning device 102 is stationary. This may advantageously expand the area which may be considered a suitable imaging location and may reduce the amount of manual adjustment performed by users, thereby reducing frustration, especially among inexperienced users. Automatic adjustment of the angle of a scan may be based on irrelevant imaging data, e.g., imaging data that does not include an anatomical structure to be imaged, and may facilitate acquisition of relevant imaging data, e.g., imaging data that includes an anatomical structure to be imaged. For example, automatic adjustment of the angle of a scan may bring into view an anatomical structure to be imaged.

Once the handheld medical scanning device 102 determines that it has reached a suitable imaging location, it may output an indication to that effect. The indication may alert the user to maintain the current position of the handheld medical scanning device. The handheld medical scanning device 102 may also output an indication when image collection has finished, which may alert a user that the handheld medical scanning device 102 may be moved from the suitable imaging position, e.g., removed from contact with a patient's body. Image collection may automatically finish in response to the handheld medical scanning device 102 determining, e.g., by analyzing received imaging data, that sufficient imaging data has been collected to perform a selected assessment, that a selected view has been obtained, that a selected imaging angle has been achieved, that a selected depth has been imaged, that a selected anatomical structure has been imaged, or any combination thereof. Image collection may finish at different times and/or in response to different determinations depending on the selected imaging procedure and/or imaging presets defining the selected imaging procedure. In other cases, imaging may continue until manually deactivated when general imaging is selected as the imaging procedure, e.g., when no imaging presets are selected.

When a selected imaging procedure includes selection of an assessment to be performed, received imaging data may be analyzed in real time or near real time to generate an assessment result. As used herein, analyzing imaging data in real time may comprise analyzing imaging data contemporaneously with reception, instantly upon reception, within a fraction of a second of reception, within a time period of reception imperceptible to an unaided human, within 1 second of reception, within two seconds of reception, within three seconds of reception, within five seconds of reception, or analyzing imaging data received as part of an imaging procedure while that imaging procedure remains ongoing.

When there is a wait time between when imaging is finished and determination of an assessment result, the handheld medical scanning device 102 may output an indication alerting a user that imaging data is being processed. The various indications described above may provide guidance to a user during imaging and may advantageously increase the likelihood that useful imaging data will be obtained and reduce the likelihood of user error, e.g., removing the handheld medical scanning device 102 before imaging is completed. Such guidance may be particularly useful to inexperienced users. Users may have the option to adjust the settings of the handheld medical scanning device 102 such that one or more of the indications is deactivated. The ability to deactivate indications may be beneficial for experienced users who may be comfortable working without the guidance provided by the indications.

Images of anatomical structures may be difficult for a non-medically trained user, such as a patient, to understand. Such users may find it easier to comprehend medical information presented in the form of assessment results, e.g., measurements and diagnoses, than to comprehend anatomical images. Accordingly, outputting an assessment result without outputting anatomical images may advantageously reduce the likelihood that a non-medically trained user will become frustrated while using the handheld medical scanning device and increases the likelihood that such a user will understand the medical information displayed.

FIG. 2 shows a diagrammatic schematic view of a handheld medical scanning device 202, according to aspects of the present disclosure. The handheld medical scanning device 202 may include a memory 208 with data 207 and a plurality of instructions 209 stored therein, an ultrasound assembly 210, a display 212, and a radiofrequency transceiver 214 each in communication with a processor 206.

The memory 208 may comprise a non-volatile memory and/or a volatile memory. The data 207 may comprise any type of data including medical data such as: imaging data, e.g., imaging data files, assessment results, diagnoses, measurements, treatment plans, medication schedules, test results, appointment schedules, progress reports, a patient history, etc. The plurality of instructions 209 may comprise instructions which, when executed by the processor 206, cause the processor to perform one or more of the techniques described herein. For example, the plurality of instructions 209 may comprise one or more of heuristic algorithms, machine learning algorithms, device positioning algorithms, algorithms for processing imaging data, algorithms for segregating relevant imaging data from irrelevant imaging data, etc.

The processor 206 may operate the ultrasound assembly 210, which may be miniaturized, and which may comprise an ultrasound transducer array in some instances, to obtain imaging data and may receive such imaging data from the ultrasound assembly 210. The processor 206 may generate images based on the received imaging data and may output such images, e.g., ultrasound images, which may comprise 3D ultrasound images, to the display 212. The processor 206 may also receive user input via the display 212. For example, the processor 206 may receive a selected imaging preset in response to a user input via the display 212. The processor 206 may operate the radiofrequency transceiver 214 to communicate with a remote medical processing system, e.g., a hospital record system or other hospital system. The radiofrequency transceiver 214 may be configured to communicate over an Institute of Electrical and Electronics Engineers (IEEE) 802.11 (WiFi) link, a Bluetooth link, a Zigbee link, an ultra-wideband (UWB) link, or over any combination thereof. In some cases, the handheld medical scanning device 202 may comprise multiple radiofrequency transceivers 214, and different radiofrequency transceivers 214 may be configured to communicate over different links. In that regard, different radiofrequency transceivers 214 may be configured to communicate over different frequencies, different time slots, etc.

Figure 3B:
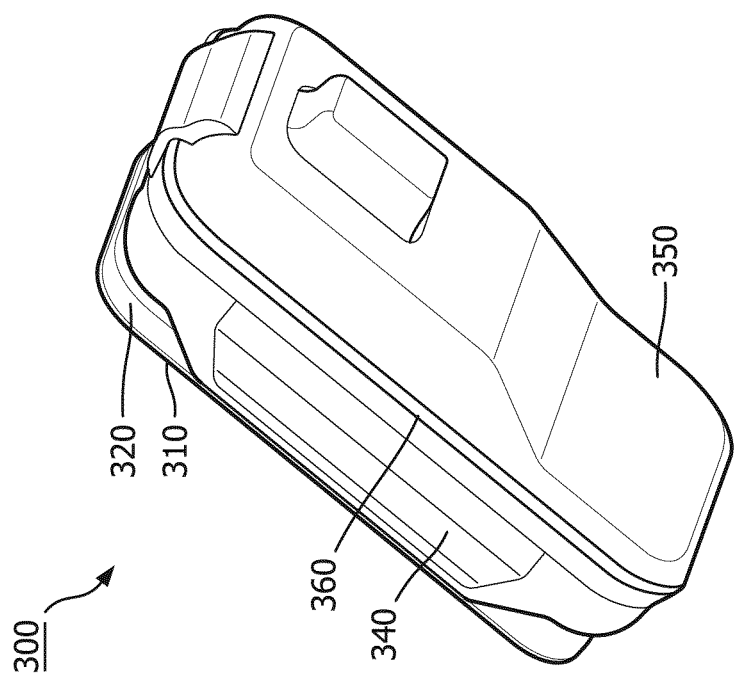
FIG. 3B is a perspective view of a rear side of a handheld ultrasound system with display retention, in accordance with at least one embodiment of the present disclosure.
Figure 3A:
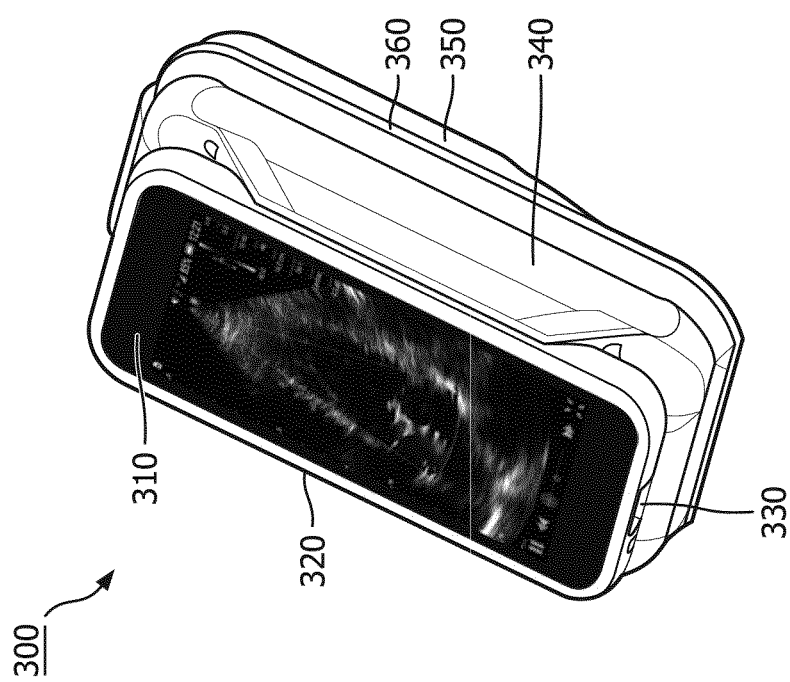
FIG. 3A is a perspective view of a front side of a handheld ultrasound system with display retention, in accordance with at least one embodiment of the present disclosure

FIG. 3A and FIG. 3B are front side and rear side perspective views, respectively, of a handheld ultrasound system 300 with display retention, in accordance with at least one embodiment of the present disclosure. Shown is the processor/display assembly 310 (e.g., a PALM COMPANION or other smartphone), held within a protective polymer phone case 320 and including a power and data socket 330 (e.g., a micro-USB socket, a USB-A socket, a USB-C socket). In other embodiments, the phone case 320 is not included. The processor/display assembly 310 fits within a press-fit feature (described below with respect to FIG. 5) of the main sensor body 340 that includes one or more raised portions positioned at least partially around a display retention region or recess. Also attached to the main scanner body 340 is a sensor cartridge body 350 (e.g., an ultrasound transducer cartridge) separated from the main sensor body 340 by a dust- and moisture-resistant gasket 360. In an example, the gasket 360 may protect electronic components within a space defined by the body 340 and/or the cartridge body 350 from exposure to dust, moisture, body fluids, acoustic matching gels, cleaning and sterilizing agents or procedures, etc. In some embodiments, the main sensor body 340 includes a communication interface that comprises electronic circuitry to facilitate communication between the sensor cartridge 350 and the processor/display assembly 310. In other embodiments, various functions of the handheld ultrasound system 300 may be performed by components coupled to and/or housed within the main sensor body 340. In some embodiments, the communication interface may include a wireless transceiver or chip configured to transmit and/or receive data wirelessly according to a wireless protocol, such as WiFi, Bluetooth, NFC, ultra-wide band (UWB), millimeter wave, and/or any other suitable protocol. In some embodiments, the interface includes an electrical interface, such as a USB interface, video graphics array (VGA) interface, serial port, ethernet interface, high definition multimedia interface (HDMI), or any other suitable electrical interface.

The three-piece architecture of the embodiment shown in FIGS. 3A and 3B advantageously permits the main scanner body 340 to be used with different sensor cartridges 350 and/or different processor/display assemblies 310, while also permitting the processor/display assembly 310 to be repositioned during use as described below, or removed and held separately for two-handed operation of the ultrasound system, with one hand holding the main scanner body 340 with the sensor cartridge 350 installed (e.g., one hand holding the main scanner body 340 and pressing the sensor cartridge 350 against the portion of the patient's anatomy intended for imaging), and the other hand holding the processor/display assembly (e.g., in a position for viewing). Two-handed operation may be advantageous for example in circumstances where, in order to image certain anatomical structures, the main sensor body 340 is held such that the sensor cartridge 350 is in contact with the patient's body near the anatomical structures. However, when two-handed operation results in the processor/display assembly 310 being held at an angle unfavorable for viewing, removing the processor/display assembly 310 and holding it with the other hand permits the clinician or other user to hold both the sensor cartridge 350 and the processor/display assembly 310 at appropriate angles for the imaging procedure. Removing the processor/display assembly 310 may also permit the clinician or other user to show live ultrasound images to the patient or to third parties as desired. In some alternative embodiments, the sensor cartridge 350 and main sensor body 340 may be combined as a single integrated unit.

With the processor/display assembly 310 held in place against the main sensor body as shown in FIGS. 3A and 3B, the system may advantageously provide a window-like viewing paradigm, where the processor/display assembly 310 shows life-size representations of the patient's anatomy located immediately beneath the handheld ultrasound system 300, such that a seemingly transparent "window into the patient" can be moved around on the patient's anatomy. For inexperienced clinicians and other users, and for patients themselves, this viewing paradigm may be more intuitive and informative than a transducer held against the patient's body and a display (e.g., showing the ultrasound images) disposed in a separate location and orientation.

Figure 14A:
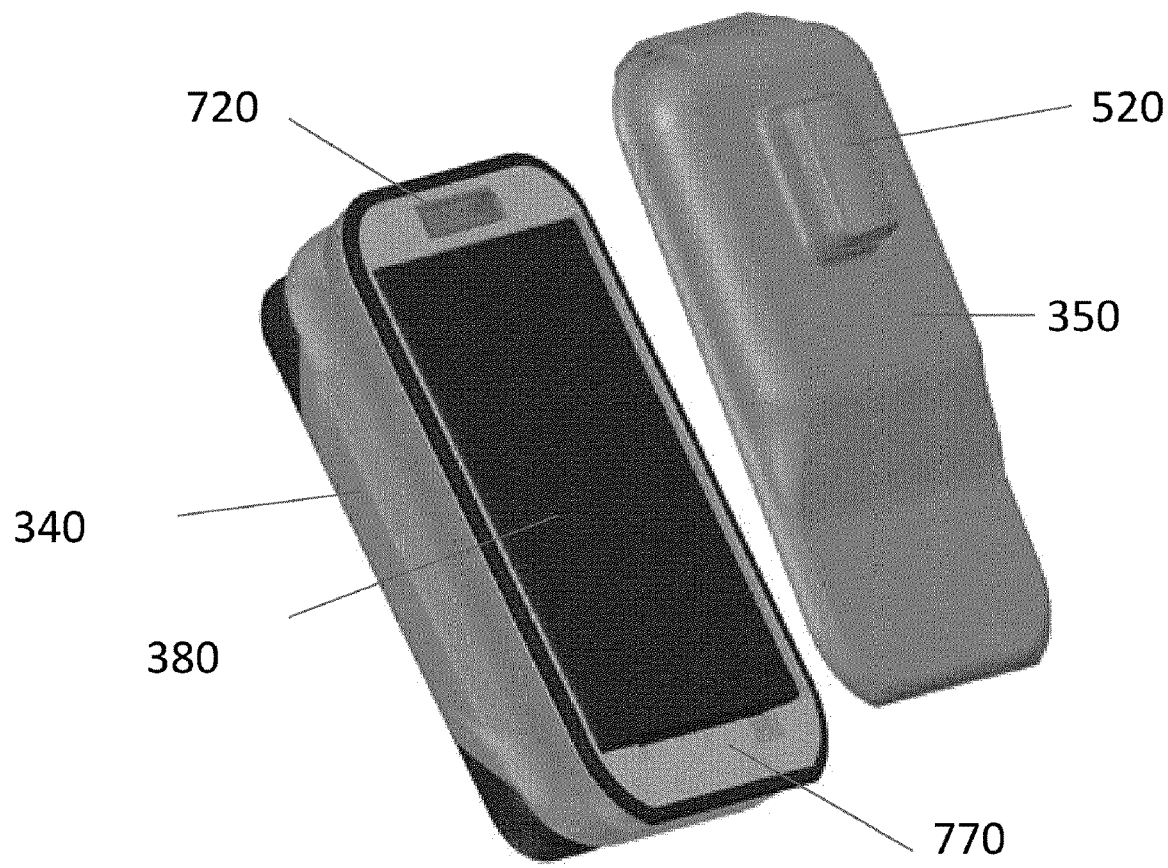
FIGS. 14A and 14B illustrate an aspect of the handheld ultrasound system highlighting the main sensor body that interfaces and couples with the sensor cartridge, according to aspects of the present disclosure.
Figure 14B:
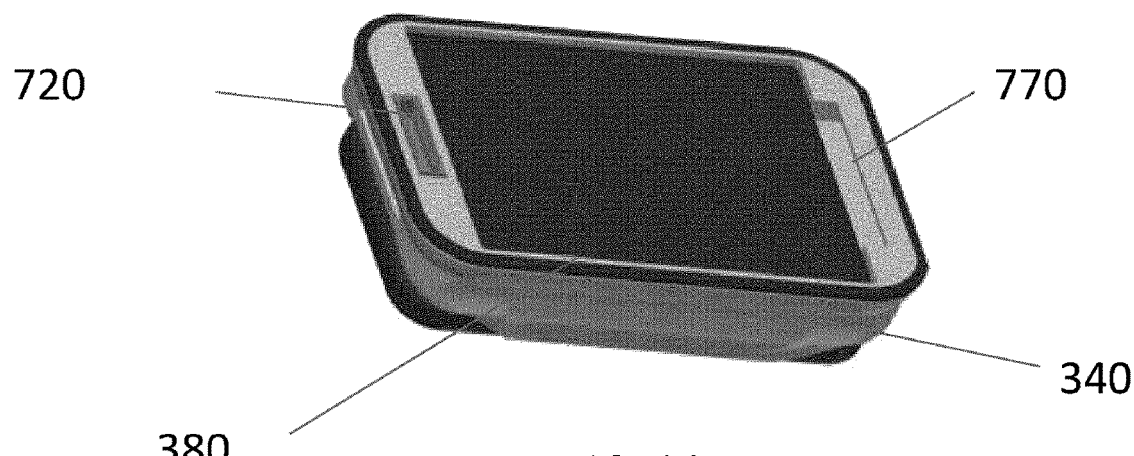

In some embodiments, the main sensor body 340 includes its own power supply (e.g., a battery), and powers the sensor cartridge 350. For example, FIGS. 14A-14B illustrate the main sensor body 340 detached from the sensor cartridge 350, in which the main sensor body shows a battery 770 disposed within the main sensor body 340. The battery 770 may be one or a plurality of batteries, and the battery 770 may be included in a recess(es) in the main sensor body 340. The battery 770 may be rechargeable directly on the main sensor body (either wireless or cord-based) or may be removable for replacement or charging on an external dock. Any type of power supply or battery may be suitable and may be selected based on the power required by the sensor cartridge 350. In other embodiments, the main sensor body 340 draws power from the processor/display assembly 310. In some embodiments, the main sensor body includes electronic circuitry, such as signal processing hardware and/or communication hardware configured to perform one or more processing and/or communication operations on ultrasound imaging signals obtained and provided by the ultrasound transducer of the sensor cartridge 350. For example, the main sensor body 340 and the sensor cartridge 350 may be configured to form a moisture- and dust-resistant enclosure inside of which various electronic components (e.g., multiplexer(s), beamformer(s), buffer(s), analog-to-digital converter(s), etc.) are contained. The electronic components may, for example, process the ultrasound imaging signals and provide image data in a format or form that is readable by the processor/display assembly 310.

Figure 4:
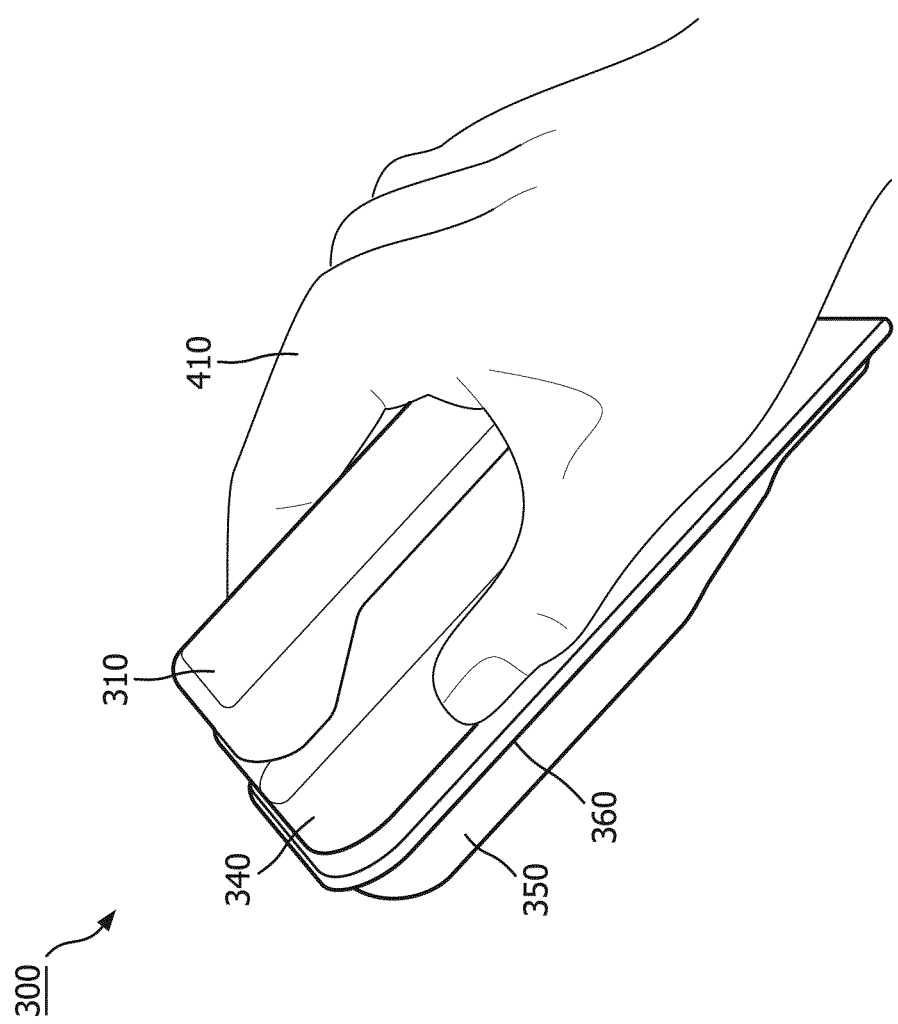
FIG. 4 is a perspective view of a handheld ultrasound system with display retention being held by a user's hand, in accordance with at least one embodiment of the present disclosure.

FIG. 4 shows a handheld ultrasound system 300 with display retention being held by a user's hand 410 in accordance with at least one embodiment of the present disclosure. When held as shown, the main scanner body 340 is capable of holding the sensor cartridge 350 against the patient's anatomy, and of holding the processor/display assembly 310 in a position where the display portion of the processor/display assembly 310 can be viewed by the clinician or other user. Depending on the exact grip position and orientation, a portion of the hand 410 may cover some, all, or none of the display portion of the processor/display assembly 310. In an example, the main sensor body may include ergonomic recesses, textured grips, or other ergonomic features to assist the thumb and fingers of the hand 410 in securely holding the main sensor body 340.

Figures 5A, 5B, 5C:
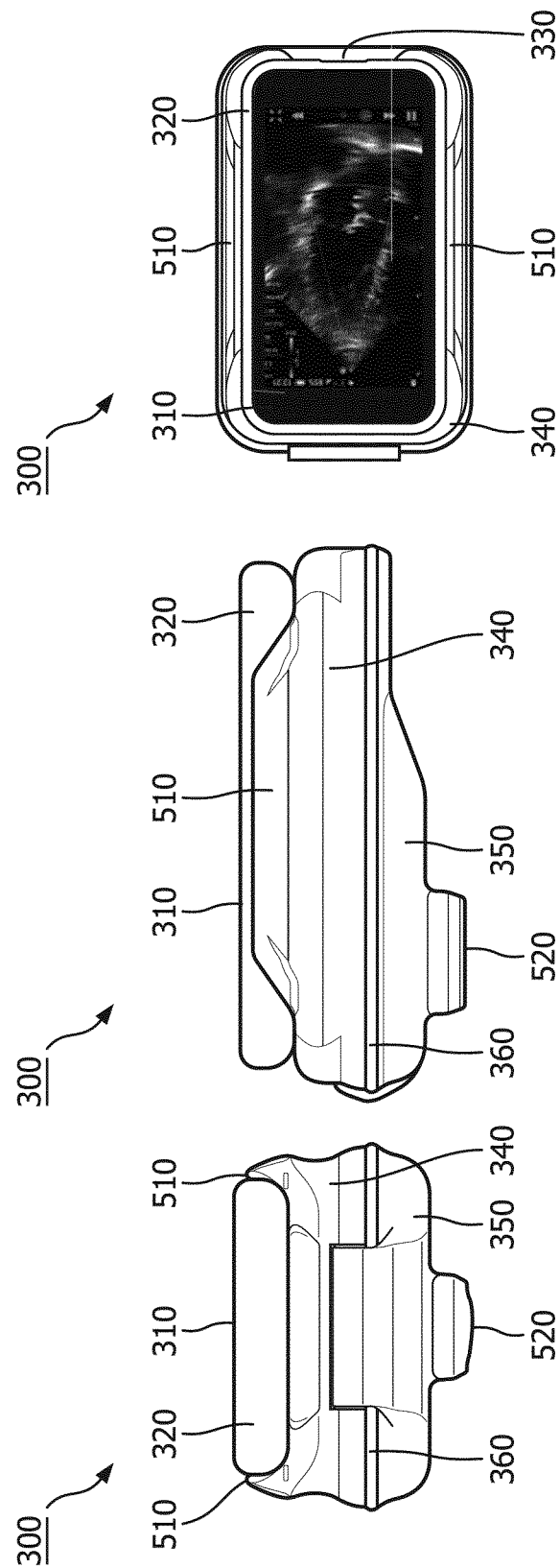
FIG. 5A is a top side elevation view of a handheld ultrasound system with display retention, in accordance with at least one embodiment of the present disclosure.
FIG. 5B is a side elevation view of a handheld ultrasound system with display retention, in accordance with at least one embodiment of the present disclosure.
FIG. 5C is an elevation view of a handheld ultrasound system with display retention, in accordance with at least one embodiment of the present disclosure.

FIG. 5A, FIG. 5B, and FIG. 5C are top, side, and front views, respectively, showing a handheld ultrasound system with press-fit display 300 in three different orientations, in accordance with at least one embodiment of the present disclosure. Visible are the processor/display assembly 310, processor/display assembly case 320, power and data socket 330, main sensor body 340, sensor cartridge 350, and gasket 360. Also visible are press-fit side rails 510 that form a recess that holds the processor/display assembly 310 in place against the main sensor body 340. The side rails 510 are retention features formed of raised portions or protrusions extending outward from the main sensor body 340, and may be sized, shaped, structurally arranged, and/or otherwise configured to retain the processor/display assembly 310 at a position and orientation with respect to the main sensor body 340. In an example, the press-fit side rails 510 are more rigid near the base and more flexible or compliant toward the ends, such that the processor/display assembly 310 can be pressed or slid into place against the main sensor body 340, and held in position by friction such that it can be readily pulled free or slid to a different position (see FIG. 8, below) by the clinician or other user, but such that it will not spontaneously fall out or slide to a different position during normal handling of the handheld ultrasound system 300.

In some embodiments, the side rails 510 include a positive curvature such that they curl partially around a lateral surface of the processor/display assembly 310 or processor/display case 320. In other embodiments, the side rails 510 have a lip for retaining the processor/display assembly 310 in place. In some embodiments, the inner shape or profile of the side rails may be selected to match a profile of the processor/display assembly 310 or processor/display case 320, such that surface-to-surface contact provides a friction-based retentive force. In some embodiments, the position of the side rails 510 may be adjustable, such that processor display assemblies 310 or processor/display cases 320 of different sizes or shapes may be used with the main sensor body 340. In some embodiments, other types of raised portions are included, such as a raised rim or edge at least partially surrounding a display retention region sized, shaped, structurally arranged, and/or otherwise configured to receive the processor/display assembly 310.

In other embodiments, in place of side rails 510, the one or more retention features 510 may comprise one or more magnets that couple, for example, to a steel plate or other paramagnetic or magnetically attractable material coupled to the processor/display assembly 310 (e.g., as part of the processor/display assembly case). Alternatively, the one or more retention features 510 may comprise a magnetically attractable material, and the processor/display assembly 310 may include one or more magnets.

Also visible is the sensor housing 520 of the sensor cartridge 350. In an example, the sensor housing 520 is pressed against the patient's body during imaging procedures. The sensor housing 520 may contain ultrasound transducers, optical coherence tomography (OCT) emitters and receivers, or other sensor components.

Figure 6:
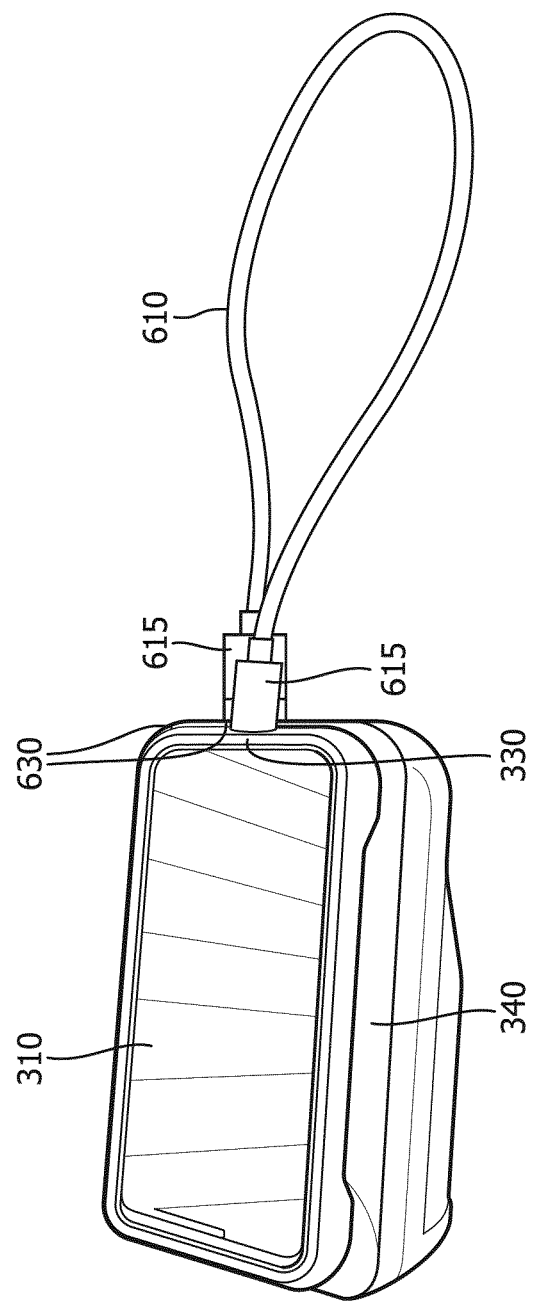
FIG. 6 is a perspective view of a handheld ultrasound system with display retention and a cable, in accordance with at least one embodiment of the present disclosure.

FIG. 6 shows a handheld ultrasound system with press-fit display 300 and cable 610 (e.g., a USB cable), in accordance with at least one embodiment of the present disclosure. The cable 610 includes connectors 615 (e.g., micro-USB, USB-A, or USB-C connectors) at both ends. The connectors 615 fit into power and data sockets 630 in both the processor/display assembly 310 and the main sensor body 340. In an example, the length of the cable 610 is selected such that it can serve as a lanyard for the handheld ultrasound system (i.e., a loop that can fit around the wrist of the user's hand 410). For example, in some embodiments, the length of the cable 610 is between about 6 inches and about 36 inches, including lengths of 6 inches, 12 inches, 18 inches, 24 inches, or any other suitable length, both greater and smaller.

FIG. 7A and FIG. 7B show a handheld ultrasound system with press-fit display and a USB cable acting as a lanyard, in accordance with at least one embodiment of the present disclosure. In the example shown in FIGS. 7A and 7B, both connectors 615 are connected to their respective sockets 630 as shown for example in FIG. 6, the length of the cable is selected such that it can fit around the wrist of the user's hand 410 as shown in FIG. 7A, and the retention force of the connections formed between the connectors 615 and the power and data sockets 630 is selected such that the connectors 615 may readily be manually disconnected from the sockets 630, but will not disconnect spontaneously from the sockets 630 if the handheld ultrasound system 300 is dropped, and its full weight is caught by the cable/lanyard 610, as shown in FIG. 7B. In that regard, in some embodiments, the retention force of the connections may be sufficient to support weights of 100 grams, 200 grams, 500 grams, 1 kilogram, 2 kilograms, 5 kilograms, or any other suitable value, both lager and smaller. This arrangement advantageously helps to protect the handheld ultrasound system 300 against damage caused by accidental drops. In some embodiments, the connectors 615 and/or sockets 630 may include retention features to facilitate a mechanical connection of the required strength to achieve this result.

Figure 8B:
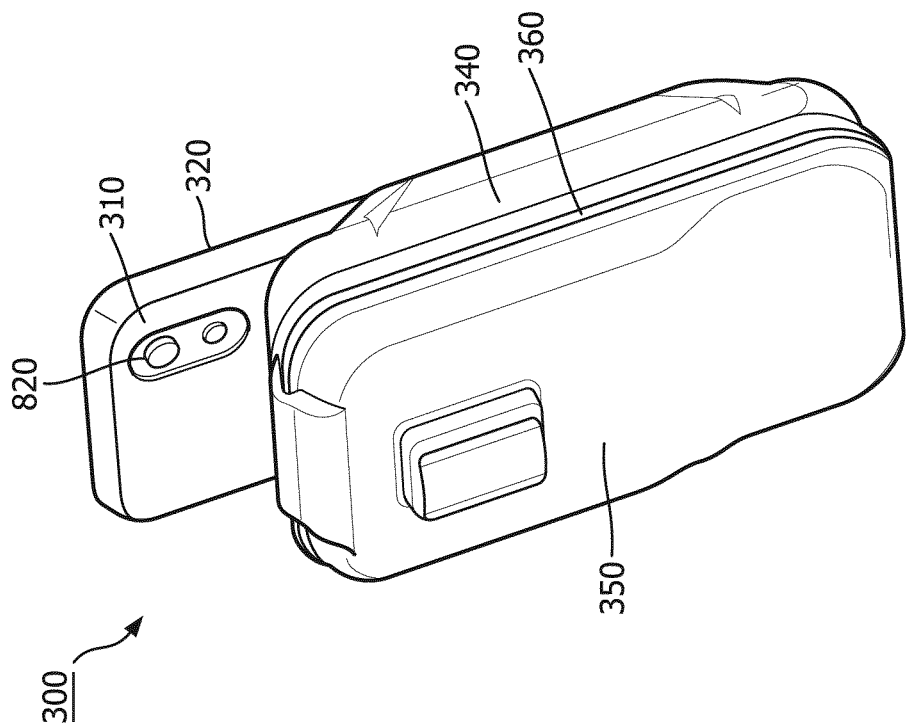
FIG. 8B is a perspective view of a rear side of a handheld ultrasound system with a repositionable press-fit display, in accordance with at least one embodiment of the present disclosure.
Figure 8A:
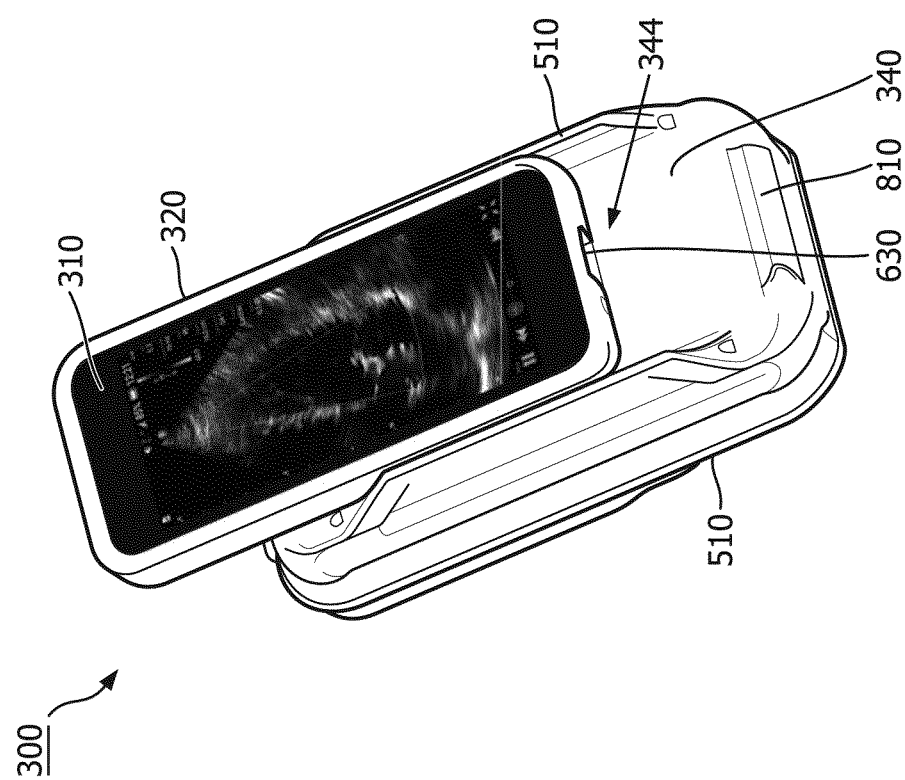
FIG. 8A is a perspective view of a front side of a handheld ultrasound system with a repositionable press-fit display, in accordance with at least one embodiment of the present disclosure.

FIG. 8A and FIG. 8B are front side and rear side perspective views, respectively, showing a handheld ultrasound system 300 with a repositionable press-fit display, in accordance with at least one embodiment of the present disclosure. Visible are the main sensor body 340, sensor cartridge 350, gasket 360, and processor/display assembly 310 in its processor/display protective case 320, which together are held in place by the press-fit rails 510. The rails 510 are positioned at least partially around a display retention region or recess 344. Whereas in FIGS. 3-7 the processor/display assembly 310 was positioned largely flush with the top and bottom edges of the main sensor body 340, FIG. 8A and FIG. 8B, show the processor/display assembly slid into a higher position. This may be done to for example to improve a viewing angle, to move the display portion of the processor/display assembly away from the user's hand, or to expose a camera 820 or other sensor within the processor/display assembly (e.g., to photograph an area of the patient's anatomy before, after, or during ultrasound imaging). In some embodiments, the processor/display assembly 310 may display co-registered camera and ultrasound images. Also visible is an optional rest or stop 810, sized and positioned such that the processor/display assembly 310 may be slid downward between the rails 510 only until it comes to rest against the rest or stop 810, at which point it cannot slide down any further. In some embodiments, the stop 810 includes a projection, such as a retention lip, or a curved protrusion to facilitate retention of the processor/display assembly 310. In some embodiments, an inner profile of the stop 810 may match an outer profile of the processor/display assembly 310 or processor/display case 320 to facilitate retention. In that regard, in some embodiments, the stop 810 comprises a curved inner surface matched to an outer surface of the processor/display assembly 310. In some embodiments, the stop may be may be sized or shaped to facilitate access to the power and data socket 630 of the processor/display assembly 310.

Figure 9B:
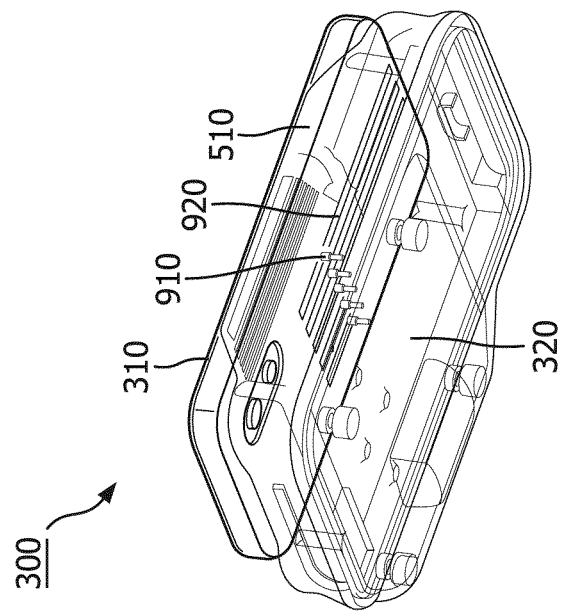
FIG. 9B is a partially transparent perspective view of a handheld ultrasound system with a repositionable press-fit display, in accordance with at least one embodiment of the present disclosure.
Figure 9A:
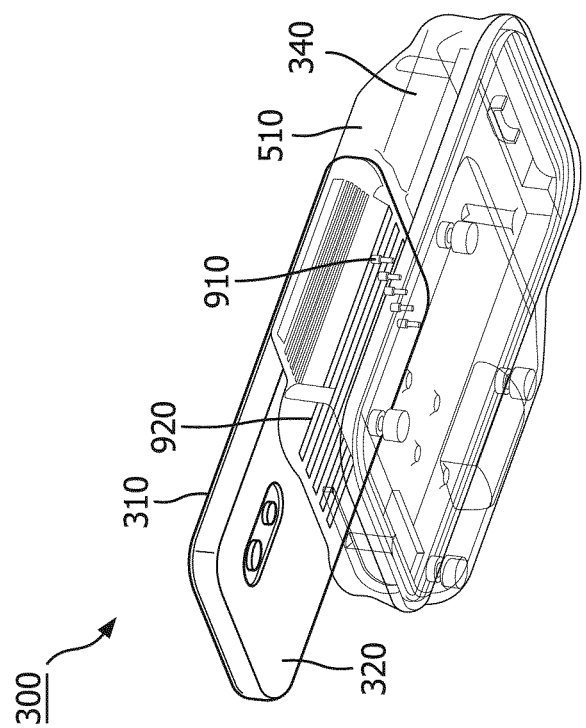
FIG. 9A is a partially transparent perspective view of a handheld ultrasound system with a repositionable press-fit display, in accordance with at least one embodiment of the present disclosure.

FIG. 9A and FIG. 9B show a partially transparent perspective view of a handheld ultrasound system 300 with a repositionable press-fit display, in accordance with at least one embodiment of the present disclosure. In the exemplary embodiment shown in FIGS. 9A and 9B, instead of the processor/display assembly 310 connecting to the main sensor body 340 via a cable, the connection is made by a set of electrical pogo pins 910 in the main sensor body 340 that respectively contact a set of conductive traces 920 formed into the processor/display protective case 320. In some aspects, this arrangement may provide a more reliable and/or higher-bandwidth connection than wireless communications such as Bluetooth. The pins 910 and conductive traces 920 are disposed such that as the processor/display assembly 310 is sild up and down between the press-fit rails 510, the pins 910 remain in contact with the conductive traces 920 across a range of different positions. The conductive traces 920 may include one or more conductive or metallic materials, such as metallic plates, foils, coatings, or other types of materials. In an example, the pins 910 are disposed below of the center of the front face of the main sensor body 340, and are sufficient in number to support a power and data connection such as a USB connection, and are spaced far enough apart to prevent electrical shorting or signal interference at the operational voltages employed by the connection.

FIG. 10A and FIG. 10B are perspective views, respectively, of a handheld ultrasound system with a removable press-fit display, in accordance with at least one embodiment of the present disclosure. Visible are the processor/display assembly 310, processor/display protective case 320, main sensor body 340, sensor cartridge 350, pogo pins 910, and conductive traces 920.

Depending on the implementation, the sensor cartridge 350 may attach to the main sensor body 340 by various means, including snap-fittings, latches, or hinges configured such that power, signal, and mechanical connection is effectuated as required for the main sensor body 340 to power, operate, and receive signals from, the sensor cartridge 350.

The sensor cartridge 350 can be manually detached from the main sensor body 340, but is retained in place such that it does not spontaneously detach under normal conditions of handling, storage, and use.

Figure 13A:
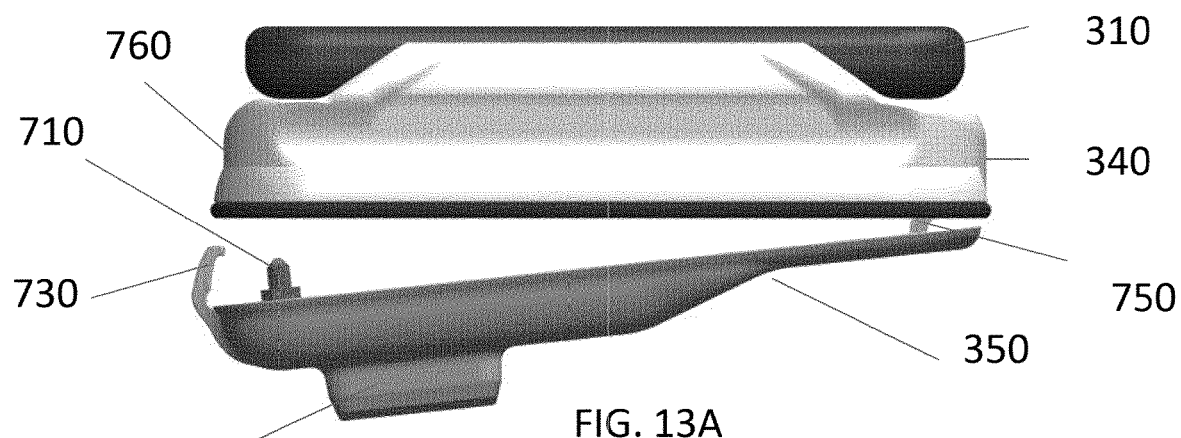
FIGS. 13A-13C illustrate an aspect of the handheld ultrasound system highlighting the sensor cartridge that interfaces and couples with the main sensor body, according to aspects of the present disclosure.
Figure 13B:
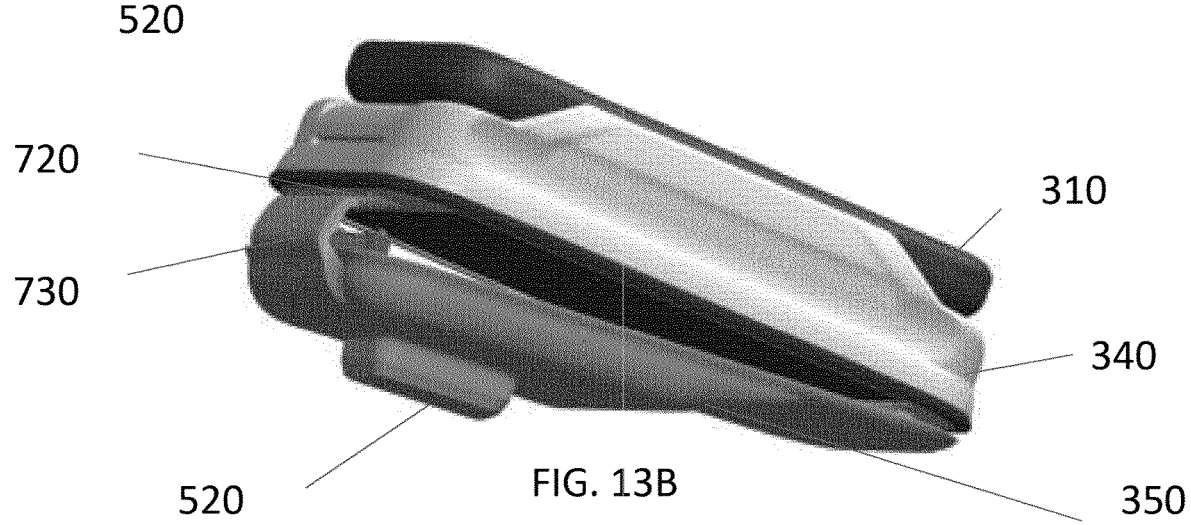
Figure 13C:
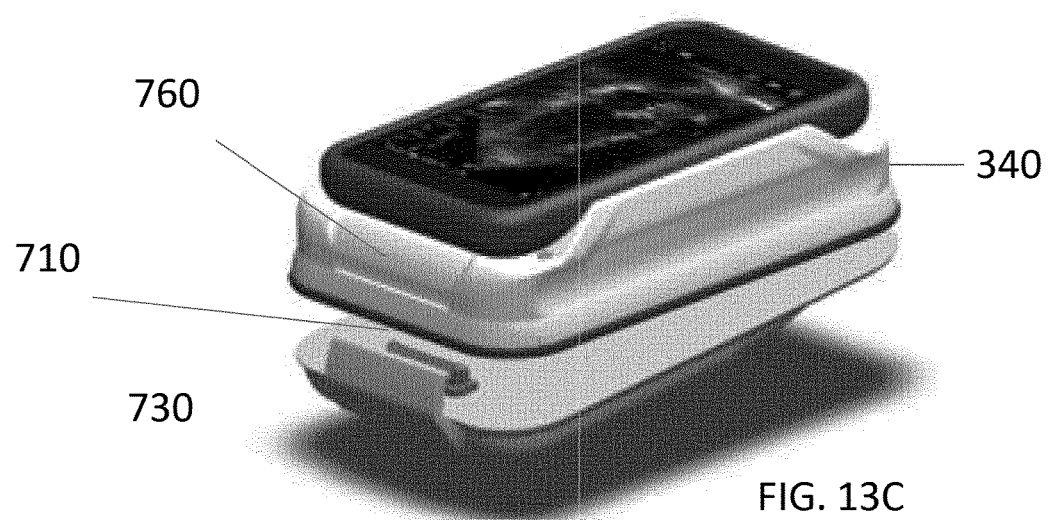

FIGS. 13A-13C provide an aspect of the handheld ultrasound system where the sensor cartridge 350 is detachable from the main sensor body 340. The sensor cartridge 350 includes one or more engagement tabs or hooks (730, 750) that are designed to mechanically couple or lock the sensor cartridge 350 to the main sensor body. The engagement tabs or hooks (730, 750) can, for example, mate with engagement indents or recesses (770, 720) for the coupling. In other embodiments (not shown), the sensor body 340 or the sensor cartridge 350 could include external side rails or lip that provide for a press-fit engagement with each other similar to that of the processor/display assembly 310 and the sensor body 310.

In addition to the mechanical coupling, the sensor cartridge 350 can be electrically coupled to the main sensor body 340. As shown, the sensor cartridge includes electrical connector 710 that pairs with electrical connector 720 on the main sensor body 720. The electrical connectors 710, 720 may include, for example, at least one of a conductive trace, a conductive pin, springs, pogos, crowns or other ports/interfaces for electrical communication. The type of interface may be chosen based on the number of signal paths needed for effective or ideal communication between the ultrasound system components. In some embodiments, the connection may be a 10, 20, 30, 40, or 50+ pin signal path connector that engages with the signal path. Ideally, the connective pair has 50 or less pins, such as a 40 pin connector.

FIGS. 14A and 14B illustrate an aspect of the handheld ultrasound system highlighting the main sensor body 340 that interfaces with the sensor cartridge 350. The battery 380 and electrical connector 720 are, for example, displayed.

Figure 15:
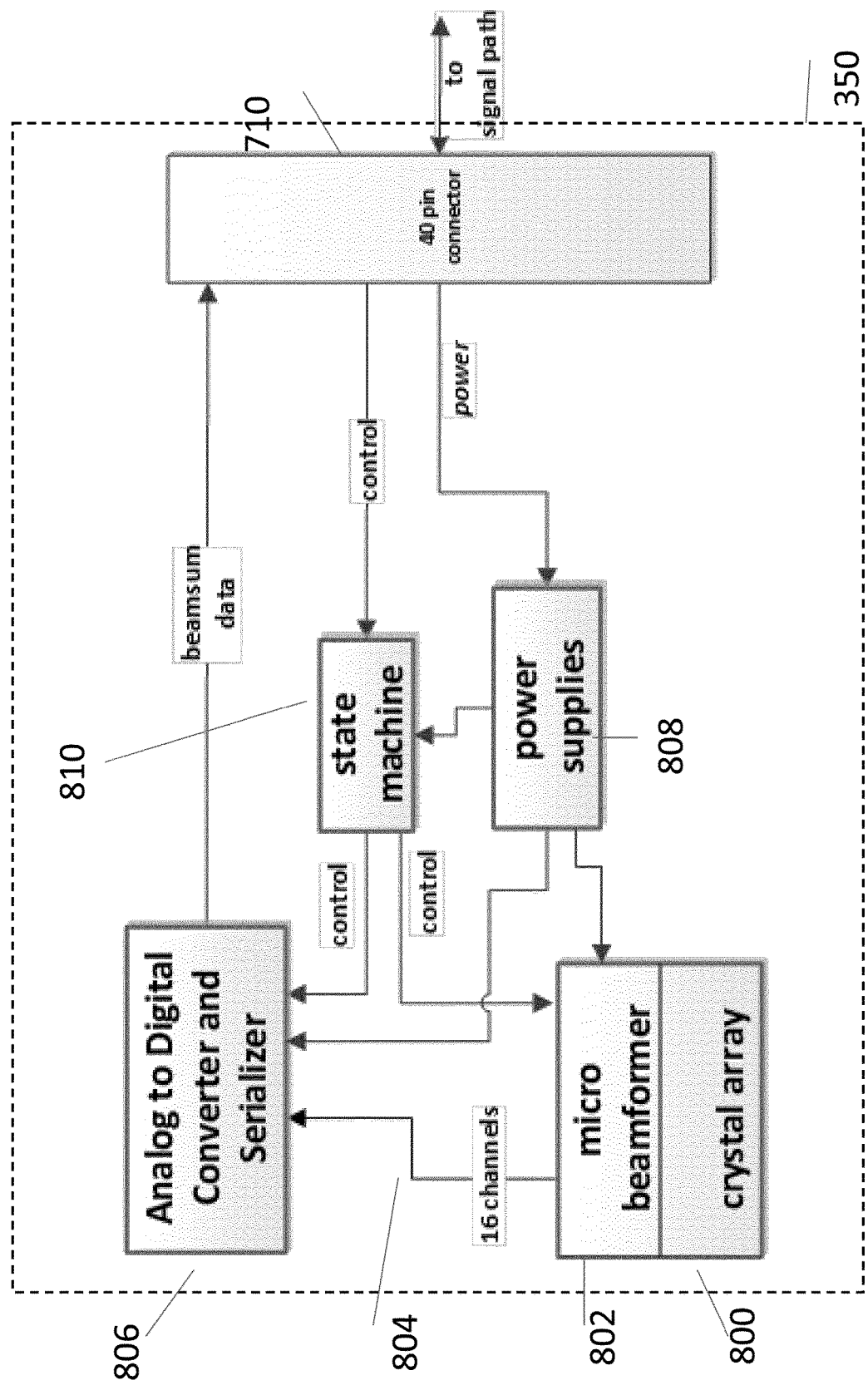
FIG. 15 provides a schematic of the circuitry associated with the sensor cartridge

FIG. 15 provides a schematic of the circuitry associated with the sensor cartridge 350, according to certain embodiments. As shown in FIG. 15, the sensor cartridge includes a transducer 800, which may include an array of transducer elements (pzt, single crystal, cmut, pmut, etc). The transducer 800 is in communication with a microbeamformer 802. The microbeamformer processes and beamforms ultrasound signals received by the transducer and transmits the signals to a A/D Converter and Serializer 806 (which may be one or several ASIC components). The beamsummed signals may be transmitted to the connector 710, which then transmits the signals to the sensor main body 340 and/or processor/display assembly 310 for additional processing of the ultrasound data for display on the processor/display assembly 310. A processor (or state machine) 810 and power supply 808 is also coupled to the A/D Converter and Serializer 806 and the beamformer to enable imaging or ultrasound operations.

Figure 11:
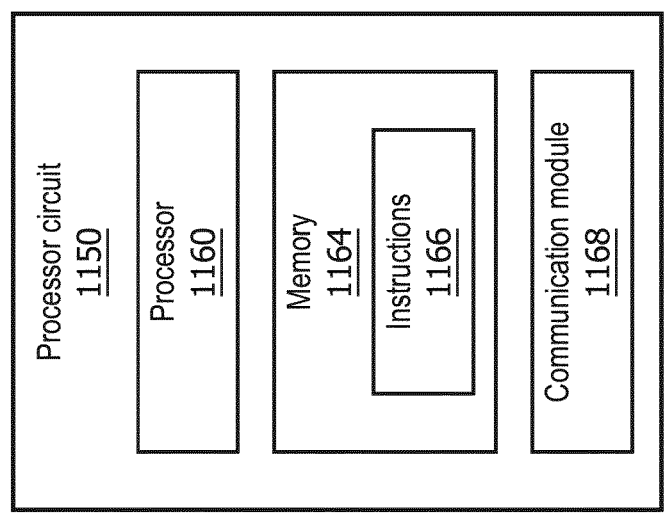
FIG. 11 is a schematic diagram of a processor circuit 1150, according to embodiments of the present disclosure.

FIG. 11 is a schematic diagram of a processor circuit 1150, according to embodiments of the present disclosure. The processor circuit 1150 may be implemented in the ultrasound imaging system 100, or other devices or workstations (e.g., third-party workstations, network routers, etc.) as necessary to implement the method. The processor circuit may comprise multiple electronics contained within the main sensor body 340, sensor cartridge 350, processor/display assembly 310, or distributed between two or more of the main sensor body 340, sensor cartridge 350, or processor/display assembly 310. As shown, the processor circuit 1150 may include a processor 1160, a memory 1164, and a communication module or assembly 1168. These elements may be in direct or indirect communication with each other, for example via one or more buses.

The processor 1160 may include a central processing unit (CPU), a digital signal processor (DSP), an ASIC, a controller, or any combination of general-purpose computing devices, reduced instruction set computing (RISC) devices, application-specific integrated circuits (ASICs), field programmable gate arrays (FPGAs), or other related logic devices, including mechanical and quantum computers. The processor 1160 may also comprise another hardware device, a firmware device, or any combination thereof configured to perform the operations described herein. The processor 1160 may also be implemented as a combination of computing devices, e.g., a combination of a DSP and a microprocessor, a plurality of microprocessors, one or more microprocessors in conjunction with a DSP core, or any other such configuration.

The memory 1164 may include a cache memory (e.g., a cache memory of the processor 1160), random access memory (RAM), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, other forms of volatile and non-volatile memory, or a combination of different types of memory. In an embodiment, the memory 1164 includes a non-transitory computer-readable medium. The memory 1164 may store instructions 1166. The instructions 1166 may include instructions that, when executed by the processor 1160, cause the processor 1160 to perform the operations described herein. Instructions 1166 may also be referred to as code. The terms "instructions" and "code" should be interpreted broadly to include any type of computer-readable statement(s). For example, the terms "instructions" and "code" may refer to one or more programs, routines, sub-routines, functions, procedures, etc. "Instructions" and "code" may include a single computer-readable statement or many computer-readable statements.

The communication module or assembly 1168 may include any electronic circuitry and/or logic circuitry to facilitate direct or indirect communication of data between the processor circuit 1150, and other processors or devices. In that regard, the communication module 1168 can be an input/output (I/O) device. In some instances, the communication module 1168 facilitates direct or indirect communication between various elements of the processor circuit 1150 and/or the ultrasound imaging system 100. The communication module 968 may communicate within the processor circuit 1150 through numerous methods or protocols. Serial communication protocols may include but are not limited to US SPI, I²C, RS-232, RS-485, CAN, Ethernet, ARINC 429, MODBUS, MIL-STD-1553, or any other suitable method or protocol. Parallel protocols include but are not limited to ISA, ATA, SCSI, PCI, IEEE-488, IEEE-1284, and other suitable protocols. Where appropriate, serial and parallel communications may be bridged by a UART, USART, or other appropriate subsystem.

External communication (including but not limited to software updates, firmware updates, or readings from the ultrasound device) may be accomplished using any suitable wireless or wired communication technology, such as a cable interface such as a USB, micro USB, Lightning, or FireWire interface, Bluetooth, WiFi, ZigBee, Li-Fi, or cellular data connections such as 2G/GSM, 3G/UMTS, 4G/LTE/WiMax, or 5G. For example, a Bluetooth Low Energy (BLE) radio can be used to establish connectivity with a cloud service, for transmission of data, and for receipt of software patches. The controller may be configured to communicate with a remote server, or a local device such as a laptop, tablet, or handheld device, or may include a display capable of showing status variables and other information. Information may also be transferred on physical media such as a USB flash drive or memory stick.

FIG. 12 is in elevation view of a handheld medical scanning device comprising a housing 1200 and a display case 1240. The housing 1200 comprises a body 1210 defining a display retention region 1220, which includes a magnet 1230 coupled to the housing 1200. The display case 1240 comprises a magnetic element 1260 coupled to a case body 1250 such that the plate 1260 is configured to align with and magnetically couple to the magnet 1230 when the case 1240 is positioned on the retention region 1220 of the housing 1200. In some embodiments, the magnetic element 1260 comprises a metal plate, such as a steel plate. In other embodiments, the magnetic element 1260 comprises a magnet. In some embodiments, the housing 1200 comprises a metal plate instead of the magnet 1230. In some embodiments, the magnet 1230 is embedded within the housing body 1210. In some embodiments, the magnet 1230 comprises a plurality of magnets positioned within the display retention region 1220. Similarly, in some embodiments, the magnetic element 1260 comprises a plurality of magnetic elements (e.g., magnetic plates) positioned at a variety of locations on the case body 1250. In some embodiments, the case 1240 is configured to releasably hold a display and/or processing module, such as a smartphone. In some embodiments, the case body 1260 is molded plastic. In some embodiments, the case body 1260 comprises an elastomeric material. In some embodiments, the housing 1200 comprises a plurality of magnets and the retention region is configured to allow for the case 1240 to be positioned at a variety of locations and/or orientations relative to the housing 1200. For example, the plurality of magnets can be distributed on the case body 1260 and/or within the display retention region 1220. In some embodiments, the display case 1240 is omitted and the magnetic element 1260 is provided on the mobile device itself (e.g., as part of the smartphone or tablet computer itself).

A number of variations are possible on the examples and embodiments described above. For example, the sensor cartridge may contain sensors of various types, whether presently known or hereinafter discovered, and may contain more than one type of sensor at a time. The system may be used for treatment (e.g., ultrasound heating) as well as imaging. The processor/display assembly may be separable for use as a smartphone or tablet computer, with all the features normally expected of such devices, or may include other health-related software, firmware, hardware, pluggable modules, etc. The technology described herein may be applied to fields other than human health care, including veterinary health care, materials inspection, archaeology, mining, and manufacturing.

The logical operations making up the embodiments of the technology described herein are referred to variously as operations, steps, objects, elements, components, or modules. Furthermore, it should be understood that these may occur or be performed in any order, unless explicitly claimed otherwise or a specific order is inherently necessitated by the claim language.

All directional references e.g., upper, lower, inner, outer, upward, downward, left, right, lateral, front, back, top, bottom, above, below, vertical, horizontal, clockwise, counterclockwise, proximal, and distal are only used for identification purposes to aid the reader's understanding of the claimed subject matter, and do not create limitations, particularly as to the position, orientation, or use of the handheld ultrasound system with display retention. Connection references, e.g., attached, coupled, connected, and joined are to be construed broadly and may include intermediate members between a collection of elements and relative movement between elements unless otherwise indicated. As such, connection references do not necessarily imply that two elements are directly connected and in fixed relation to each other. The term "or" shall be interpreted to mean "and/or" rather than "exclusive or." Unless otherwise noted in the claims, stated values shall be interpreted as illustrative only and shall not be taken to be limiting.

The above specification, examples and data provide a complete description of the structure and use of exemplary embodiments of the handheld ultrasound system with display retention as defined in the claims. Although various embodiments of the claimed subject matter have been described above with a certain degree of particularity, or with reference to one or more individual embodiments, those skilled in the art could make numerous alterations to the disclosed embodiments without departing from the spirit or scope of the claimed subject matter.

Still other embodiments are contemplated. It is intended that all matter contained in the above description and shown in the accompanying drawings shall be interpreted as illustrative only of particular embodiments and not limiting. Changes in detail or structure may be made without departing from the basic elements of the subject matter as defined in the following claims.

What is claimed is:

1. A handheld ultrasound scanning device, comprising:
a main body housing configured for handheld use, wherein the main body housing comprises a first side and a different second side; and
an ultrasound transducer coupled to the second side of the main body housing and configured to obtain ultrasound data,
wherein the main body housing comprises a communication interface communicatively coupled to the ultrasound transducer and configured to transmit the ultrasound data obtained by the ultrasound transducer to a processor and display assembly configured to display ultrasound images representative of the ultrasound data, wherein the communication interface is configured to maintain communication with the processor and display assembly when the processor and display assembly is received within the retention region and when the processor and display assembly is removed from the retention region,
wherein the first side of the main body housing includes one or more retention features at least partially around a retention region, wherein the retention region is sized and shaped to receive the processor and display assembly, and wherein the one or more retention features are configured to retain the processor and display assembly in contact with the main body housing at a position and orientation relative to the main body housing, such that the processor and display assembly can be removed from the retention region; and
a power or data cable coupling the main body housing to the processor and display assembly, wherein the power or data cable is connected to a first power or data socket in the main body housing to form a first power or data connection, and wherein the power or data cable is connected to a second power or data socket in the processor and display assembly to form a second power or data connection, wherein the first power or data connection of the power or data cable and the first power or data socket comprises a first retention force, wherein the second power or data connection of the power or data cable and the second power or data socket comprises a second retention force, wherein the first retention force and the second retention force exceed a weight of the handheld ultrasound scanning device.

2. The handheld ultrasound scanning device of claim 1, further comprising the processor and display assembly, wherein the processor and display assembly comprises a smartphone or tablet computer.

3. The handheld ultrasound scanning device of claim 1, wherein the one or more retention features are configured to slidably retain the processor and display assembly such that the processor and display assembly can be repositioned at a plurality of positions relative to the main body housing.

4. The handheld ultrasound scanning device of claim 3, wherein the one or more retention features slidably retain the processor and display assembly such that the processor and display assembly can be repositioned to expose a camera of the processor and display assembly.

5. The handheld ultrasound scanning device of claim 3, wherein the one or more retention features comprise a stop positioned to arrest sliding of the processor and display assembly in a first direction while permitting the sliding of the processor and display assembly in an opposite second direction.

6. The handheld ultrasound scanning device of claim 5, wherein the stop comprises a retention lip.

7. The handheld ultrasound scanning device of claim 1, wherein the one or more retention features comprise a plurality of rails projecting from the first side of the main body housing and positioned on opposing sides of the retention region.

8. The handheld ultrasound scanning device of claim 7, wherein at least one rail comprises a retention lip or a curved inner surface matched to an outer surface of the processor and display assembly.

9. The handheld ultrasound scanning device of claim 1, wherein the one or more retention features comprise one or more magnets, and wherein the processor and display assembly comprises a magnetically attractable material.

10. The handheld ultrasound scanning device of claim 1, wherein the one or more retention features comprise a magnetically attractable material, and wherein the processor and display assembly comprises one or more magnets.

11. The handheld ultrasound scanning device of claim 1, wherein the power or data cable comprises a length that wraps around a wrist of a user when connected to the first power or data socket and the second power or data socket.

12. The handheld ultrasound scanning device of claim 1, wherein the communication interface comprises at least one of a conductive pin or a conductive trace configured to be in electrical communication with at least one of a conductive trace or a conductive pin of the processor and display assembly.

13. The handheld ultrasound scanning device of claim 1, wherein the communication interface is configured to transmit the ultrasound data to the processor and display assembly by a wireless link.

14. The handheld ultrasound scanning device of claim 1, further comprising an ultrasound transducer cartridge comprising a cartridge body removably coupled to the second side of the main body housing, wherein the ultrasound transducer is coupled to a side of the cartridge body.

15. The handheld ultrasound scanning device of claim 14, wherein the cartridge body is configured to form a moisture and dust-resistant enclosure with the main body housing.

16. The handheld ultrasound scanning device of claim 1, further comprising processing circuitry contained within the main body housing and communicatively coupled to the communication interface and the ultrasound transducer.

17. A handheld ultrasound device, comprising:
a main body housing configured for handheld use, wherein the main body housing comprises:
two or more side rails protruding from a front surface of the main body housing and positioned on opposing sides of a retention region, wherein the retention region is configured to receive a processor and display assembly;
a communication interface configured to establish an electrical connection with a corresponding plurality of conductive traces coupled to the processor and display assembly when the processor and display assembly is positioned within the retention region, wherein the communication interface is configured to maintain communication with the processor and display assembly when the processor and display assembly is received within the retention region and when the processor and display assembly is removed from the retention region; and
processing circuitry contained within the main body housing and communicatively coupled to the communication interface; and
an ultrasound transducer cartridge coupled to a rear surface of the main body housing, wherein the ultrasound transducer cartridge comprises an ultrasound transducer positioned on a rear side of the ultrasound transducer cartridge,
wherein the ultrasound transducer is configured to emit ultrasonic energy and provide, to the processing circuitry, ultrasound signals representative of echoes of the ultrasonic energy, and
wherein the processing circuitry is configured to perform signal processing on the ultrasound signals to provide data to the processor and display assembly, and
a power or data cable coupling the main body housing to the processor and display assembly, wherein the power or data cable is connected to a first power or data socket in the main body housing to form a first power or data connection, and wherein the power or data cable is connected to a second power or data socket in the processor and display assembly to form a second power or data connection, wherein the first power or data connection of the power or data cable and the first power or data socket comprises a first retention force, wherein the second power or data connection of the power or data cable and the second power or data socket comprises a second retention force, wherein the first retention force and the second retention force exceed a weight of the handheld ultrasound scanning device.

18. A handheld ultrasound scanning device, comprising:
a main body housing configured for handheld use, wherein the main body housing comprises a first side and a different second side, the first side comprising a first electrical connector and a first mechanical connector;
a sensor cartridge configured to removably couple with the first side of the main body housing, the sensor cartridge comprising a second electrical connector and a second mechanical connector, wherein the second electrical connector mates with the first electrical connector and the second mechanical connector mates with the first mechanical connector, the sensor cartridge further comprising:
a transducer configured to send and receive ultrasound signals;
circuitry configured to process the received ultrasound signals and transfer the processed signals to the main body housing via the first and second electrical connectors;
a processor and display assembly coupled to the second side of the main body housing and configured to receive the processed signals, generate a clinical parameter from the processed signals, and display the clinical parameter to a user of the handheld ultrasound system, wherein the coupling is configured to maintain communication with the processor and display assembly when the processor and display assembly is received within a retention region and when the processor and display assembly is removed from the retention region; and
a power or data cable coupling the main body housing to the processor and display assembly, wherein the power or data cable is connected to a first power or data socket in the main body housing to form a first power or data connection, and wherein the power or data cable is connected to a second power or data socket in the processor and display assembly to form a second power or data connection, wherein the first power or data connection of the power or data cable and the first power or data socket comprises a first retention force, wherein the second power or data connection of the power or data cable and the second power or data socket comprises a second retention force, wherein the first retention force and the second retention force exceed a weight of the handheld ultrasound scanning device.

19. The handheld ultrasound scanning device of claim 18, wherein the clinical parameter includes an image, a measurement or both.

* * * * *